United States Patent [19]

Morgan et al.

[11] Patent Number: 5,378,803

[45] Date of Patent: Jan. 3, 1995

[54] AZOLE-FUSED PEPTIDES AND PROCESSES FOR PREPARATION THEREOF

[75] Inventors: Barry A. Morgan, Colonie; Thomas D. Gordon; Philip E. Hansen, both of Schodack; Jasbir Singh, Albany, all of N.Y.

[73] Assignee: Sterling Winthrop Inc., New York, N.Y.

[21] Appl. No.: 912,949

[22] Filed: Jul. 10, 1992

Related U.S. Application Data

[63] Continuation of Ser. No. 131,706, Dec. 11, 1987, abandoned.

[51] Int. Cl.$^6$ .......................... C07K 5/08; C07K 5/10; C07K 5/12; C07K 7/06
[52] U.S. Cl. ..................... 530/317; 530/321; 530/328; 530/329; 530/330; 530/331
[58] Field of Search ................ 530/317, 321, 328–331

[56] References Cited

U.S. PATENT DOCUMENTS 4,472,305  9/1984  Hansen et al. .................. 530/329

OTHER PUBLICATIONS

Sandberg et al., J. Med. Chem., vol. 25, No. 9, pp. 1009–1015, 1982.
Pettit et al., J. Am. Chem. Soc., vol. 104, pp. 905–907, 1982.
Oikawa et al., J. Org. Chem., vol. 42, pp. 1213–1216, 1977.
Stork et al., J. Org. Chem., vol. 41, pp. 3491–3493, 1986.
O'Donnell et al., Tet. Let., No. 30, pp. 2641–2644, 1978.
Nakajima et al., Peptide Chemistry 1982, Protein Research Foundation, Osaka, Japan, pp. 19–24, 1983.

*Primary Examiner*—Lester L. Lee
*Attorney, Agent, or Firm*—Liza D. Hohenschutz; Arthur H. Rosenstein; Paul E. Dupont

[57] ABSTRACT

Azole-fused peptides useful as Substance P antagonists and analgesics, for example

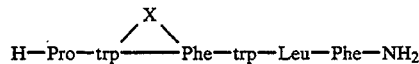

wherein

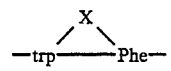

represents

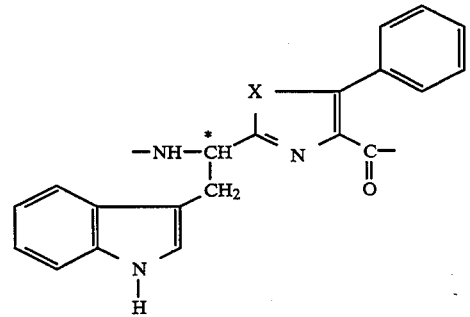

wherein X is O, S or NH and * is D, or as intermediates therefor are prepared by azole and peptide forming methods.

34 Claims, No Drawings

5,378,803

AZOLE-FUSED PEPTIDES AND PROCESSES FOR PREPARATION THEREOF

CROSS-REFERENCE TO RELATED APPLICATION

This application is a continuation of my prior copending application Ser. No. 07/131,706 filed Dec. 11, 1987 and now abandoned.

BACKGROUND OF THE INVENTION

FIELD OF THE INVENTION

The invention relates to azole-fused peptides, which are useful as Substance P antagonists and analgesics or as synthetic intermediates therefor and to processes for preparation thereof.

INFORMATION DISCLOSURE STATEMENT

Substance P (SP) is an endogenous undecapeptide amide and a putative neurotransmitter of mammalian central nervous systems (Sandberg et al., J. Med. Chem., vol. 25, no. 9, pp. 1009–1015, 1982) having the following structural formula, wherein the amino acid units are numbered from 1 through 11 beginning with the N-terminal amino acid:

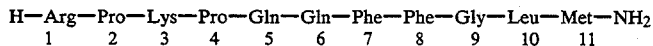

The hexapeptide amide having the structural formula

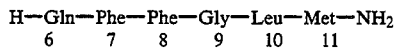

is referred to as SP$_{6-11}$.

Hansen et al. U.S. Pat. No. 4,472,305 issued Sep. 18, 1984 describes Substance P agonist and/or antagonist hexapeptide amides related to SP$_{6-11}$ including the product of example 17 having in its free base form the structural formula

Numerous naturally occurring thiazole-fused peptides are known, all of which are putatively biosynthesized from cystiene and therefore unsubstituted at the 5-position of the thiazole ring. For example, Pettit et al. (J. Am. Chem. Soc., vol. 104, pp. 905–907, 1982) describes a cyclic heptapeptide called dolastatin 3 and ascribed the structural formula

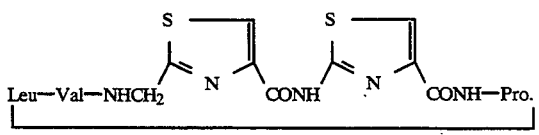

There are no known thiazole-fused peptides which are substituted at the 5-position of the thiazole ring. No oxazole-fused or imidazole-fused peptides are known.

Oikawa et al. (J. Org. Chem., vol. 42, pp. 1213–1216, 1977) describes preparation of methyl 5-(3-indolyl)-2-methyloxazole-3-carboxylate in 33% yield by oxidation of methyl 2-acetamido-3-(3-indolyl)propionate with DDQ in tetrahydrofuran. Use of aqueous tetrahydrofuran gave methyl 2-acetamido-3-(3-indolyl)-3-oxopropionate in 84% yield. Preparation of the corresponding thiazole or imidazole is not described.

Stork et al. (J. Org. Chem., vol. 41, pp. 3491–3493, 1986) describes alkylation of the benzaldehyde Schiff base of ethyl glycinate in preparing ethyl α-alkylglycinates. O'Donnell et al. (Tet. Let., no. 30, pp. 2641–2644, 1978) describes alkylation of the benzophenone Schiff base of ethyl glycinate in preparing α-alkylglycines. Acylation of the benzaldehyde and benzophenone Schiff bases of glycine esters is not known.

Nakajima et al. (Peptide Chemistry 1982, Protein Research Foundation, Osaka, Japan, pp. 19–24) describes formation of oxazoline-fused peptides using triphenylphosphine and diethyl azodicarboxylate, for example,

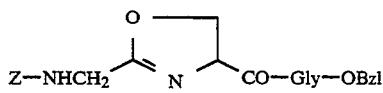

from Z-Gly-Ser-Gly-OBzl wherein Ser represents L-seryl and Bzl represents benzyl.

SUMMARY OF THE INVENTION

In a composition of matter aspect the invention is the azole-fused peptide having the structural formula

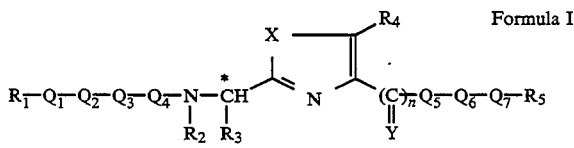

wherein
Q$_1$ is L-prolyl or a direct linkage;
Q$_2$ is L-prolyl, D-tryptophyl or a direct linkage;
Q$_3$ is L-prolyl, D-tryptophyl, L-phenylalanyl, R-(2,3,4,9-tetrahydro-1H-pyrido[3,4-b]indol-2-yl-3-carbonyl a direct linkage;
Q$_4$ is L-prolyl, D-tryptophyl, L-phenylalanyl or a direct linkage;
Q$_5$ is D-tryptophyl or L-phenylalanyl or a direct linkage;
Q$_6$ is L-leucyl, L-methionyl or a direct linkage;
Q$_7$ is L-phenylalanyl, N-methyl-L-phenylalanyl, L-methionyl or a direct linkage;
R$_1$ is a hydrogen atom, (phenylmethoxy)carbonyl or (1,1-dimethylethoxy)carbonyl;
R$_2$ taken alone is a hydrogen atom;
R$_3$ taken alone is 1-methylethyl, 2-methylpropyl, 4-aminobutyl, phenylmethyl, 4-hydroxyphenylmethyl, pyridylmethyl, or (1H-indol-3-yl)methyl; or
R$_2$ taken together with N, CH and R$_3$ is (2,3,4,9-tetrahydro-1H-pyrido[3,4-b]indol-2,3-diyl); R$_4$ is ethyl, propyl, 1-methylethyl, methylthiomethyl, ethylthiomethyl, phenyl, 4-hydroxyphenyl, pyridyl, or 1H-indol-3-yl; R$_5$ is a hydrogen atom when n is 0 and Q$_5$, Q$_6$ and Q$_7$ are each a direct linkage; hydroxy or an alkali metal salt thereof, methoxy, ethoxy, 1,1-dimethylethoxy, amino, methylamino, dimethylamino, 2-(dimethylamino)-ethylamino, (2-amino-3-phenylpropyl)amino or N-methyl-2-phenylethylamino when Y is oxo and n is 1; or hydroxy or an alkali metal salt thereof, amino, methylamino, dimethylamino, 2-(dimethylamino)ethylamino, (2-amino-3-phenylpropyl)amino, 2-amino-1-(phenylmethyl)ethylamino, or N-methyl-2-phenylethylamino when Y is two separately bonded hydrogen atoms, n is 1 and $Q_5$, $Q_6$ and $Q_7$ are each a direct linkage;

X is oxa, thia or imido;
Y is oxo or two separately bonded hydrogen atoms;
n is 0 or 1; and
* is L or D; or
a pharmaceutically acceptable acid addition salt and/or solvate thereof.

The azole-fused peptides of Formula I are useful as Substance P antagonists and analgesics or as synthetic intermediates therefor.

In a first process aspect the invention is the process of preparing an azole-fused peptide of Formula I wherein X is thia which comprises the step of oxidizing with 2,3-dichloro-5,6-dicyanoquinone in an inert solvent or solvent mixture the corresponding peptide having the structural formula

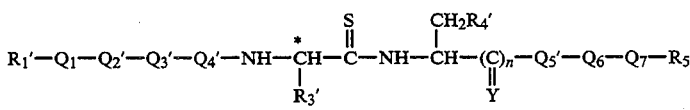

Formula II wherein $Q'_2$ is L-prolyl or a direct linkage; $Q'_3$ is L-prolyl, L-phenylalanyl or a direct linkage; $Q'_4$ is L-prolyl, L-phenylalanyl or a direct linkage; $Q'_5$ is L-phenylalanyl or a direct linkage; $R'_1$ is the same as defined for $R_1$ in Formula I except that $R'_1$ cannot be a hydrogen atom when $Q_1$, $Q'_2$, $Q'_3$ and $Q'_4$ are each a direct linkage; $R'_3$ is 1-methylethyl, 2-methylpropyl or phenylmethyl; $R_4$ is 1H-indol-3-yl; and $Q_1$ $Q_6$, $Q_7$, $R_5$, Y, n and * are the same as defined for Formula I.

In a second process aspect the invention is the process of preparing a peptide having the structural formula

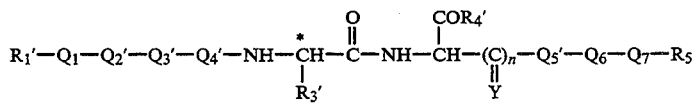

Formula III which comprises the step of oxidizing with 2,3-dichloro-5,6-dicyanoquinone in an inert aqueous solvent or solvent mixture the corresponding peptide having the structural formula

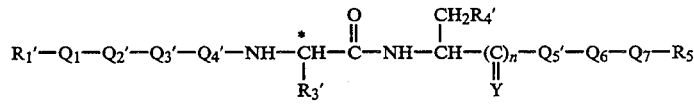

Formula IV wherein
$Q'_2$ is L-prolyl or a direct linkage;
$Q'_3$ is L-prolyl, L-phenylalanyl or a direct linkage;
$Q'_4$ is L-prolyl, L-phenylalanyl or a direct linkage;
$Q'_5$ is L-phenylalanyl or a direct linkage; $R'_1$ is the same as defined for $R_1$ in Formula I except that $R'_1$ cannot be a hydrogen atom when $Q_1$, $Q'_2$, $Q'_3$ and $Q'_4$ are each a direct linkage; $R'_3$ is 1-methylethyl, 2-methylpropyl or phenylmethyl; $R'_4$ is 1H-indol-3-yl; and $Q_1$, $Q_6$, $Q_7$, $R_5$, Y, n and * are the same as defined for Formula I.

In a third process aspect the invention is the process of preparing a dipeptide having the structural formula

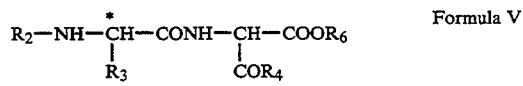

Formula V which comprises the steps of acylating with the corresponding acid chloride having the structural formula $R_4$—COCl  Formula VI using an alkali metal alkoxide in an inert solvent mixture the corresponding iminoester having the structural formula phenyl-$CR_7$=N—$CH_2$—$COOR_6$  Formula VII and then hydrolyzing the resulting corresponding acyliminoester having the structural formula phenyl-$CR_7$=N—CH($COR_4$)—$COOR_6$  Formula VIII with an aqueous mineral acid to form the corresponding acylaminoester having the structural formula $R_4$—CO—CH($NH_2$)—$COOR_6$  Formula IX and then condensing the acylaminoester of Formula IX with the corresponding amino acid having the structural formula

Formula X by a peptide forming method, concomitantly protecting and deprotecting any free amino or hydroxy, wherein $R_2$, $R_3$, $R_4$ and * are the same as defined for Formula I, $R_6$ is methyl, ethyl or 1,1-dimethylethyl and $R_7$ is a hydrogen atom or phenyl.

In a fourth process aspect the invention is the process of preparing an azole-fused peptide of Formula I wherein X is oxa which comprises the step of cyclizing with triphenylphosphine or tributylphosphine, diazabicycloundecene or diazabicyclononene and carbon tetrachloride or chloranil in acetonitrile as solvent or in a solvent mixture of acetonitrile and pyridine the corresponding dipeptide having the structural formula

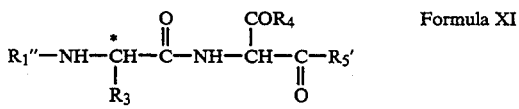
Formula XI or the corresponding aminoketoamide having the structural formula

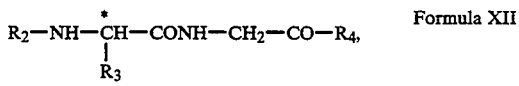
Formula XII concomitantly protecting and deprotecting any free amino or hydroxy, wherein $R_2$, $R_3$, $R_4$ and * are the same as defined for Formula I, $R''_1$ is (phenylmethoxy)carbonyl and $R'_5$ is methoxy, ethoxy or 1,1-dimethylethoxy to form the corresponding oxazole-fused dipeptide of Formula I wherein $Q_1$, $Q_2$, $Q_3$, $Q_4$, $Q_5$, $Q_6$ and $Q_7$ are each a direct linkage, $R_1$ is (phenylmethoxy)carbonyl, $R_2$ is a hydrogen atom, $R_5$ is hydrogen, methoxy or ethoxy, X is oxa, Y is oxo and n is 0 or 1.

In a fifth process aspect the invention is the process of preparing an azole-fused peptide of Formula I wherein X is thia which comprises the step of condensing the corresponding aminothioamide having the structural formula

Formula XIII with the corresponding ketochloroester having the structural formula $$R''_4\text{—CHCl—CO—COOR}_8 \quad \text{Formula XIV}$$

or a mixture thereof with the corresponding epoxychloroester having the structural formula

Formula XV in an inert solvent or solvent mixture with heating to form the corresponding azole-fused peptide of Formula I, concomitantly protecting and deprotecting any free amino or hydroxy, wherein $Q_1$, $Q_2$, $Q_3$, $Q_4$, $Q_5$, $Q_6$ and $Q_7$ are each a direct linkage, $R_1$ is (phenylmethoxy)carbonyl, $R_5$ is methoxy or ethoxy, X is thia, Y is oxo, n is 1 and * is L or D and wherein in Formulas XIII, XIV and XV $R''_1$ is (phenylmethoxy)carbonyl, $R_2$ and $R_3$ are the same as defined for Formula I, $R''_4$ n is ethyl, propyl, 1-methylethyl, phenyl or 4-hydroxyphenyl, $R_8$ is methyl or ethyl and * is L or D.

In a sixth process aspect the invention is the process of preparing an azole-fused peptide of Formula I wherein X is thia and corresponding to a peptide of Formula III, a dipeptide of Formula V or an aminoketoamide of Formula XII which comprises the step of cyclizing the corresponding peptide of Formula III, dipeptide of Formula V or aminoketoamide of Formula XII with an amide thionating reagent in an inert solvent with heating.

In a seventh process aspect the invention is the process of preparing an azole-fused peptide of Formula I wherein X is imido and corresponding to a peptide of Formula III, a dipeptide of Formula V or an aminoketoamide of Formula XII which comprises the step of cyclizing the corresponding peptide of Formula III, dipeptide of Formula V or aminoketoamide of Formula XI I with ammonia or an ammonium salt in acetic acid or a mixture of acetic acid and an inert solvent with heating.

In an eighth process aspect the invention is the process of preparing an azole-fused peptide of Formula I which comprises the step of condensing the corresponding azole-fused peptide of Formula I wherein any or all of $Q_1$, $Q_2$, $Q_3$, $Q_4$, $Q_5$, $Q_6$ and $Q_7$ is a direct linkage with any of the amino acid or peptide moieties $Q_2$, $Q_3$, $Q_4$, $Q_5$, $Q_6$, $Q_7$, $Q_1$-$Q_2$, $Q_2$-$Q_3$, $Q_3$-$Q_4$, $Q_5$-$Q_6$, $Q_6$-$Q_7$, $Q_1$-$Q_2$-$Q_3$, $Q_2$-$Q_3$-$Q_4$, $Q_5$-$Q_6$-$Q_7$ and $Q_1$-$Q_2$-$Q_3$-$Q_4$ wherein $Q_1$, $Q_2$, $Q_3$, $Q_4$, $Q_5$, $Q_6$ and $Q_7$ of each said moiety is other than a direct linkage by a peptide forming method, concomitantly protecting and deprotecting the N-terminal α-amino and the C-terminal carboxyl as required.

In a ninth process aspect the invention is the process of preparing an azole-fused peptide of Formula I wherein Y is two separately bonded hydrogen atoms, n is 1 and $Q_1$, $Q_2$, $Q_3$, $Q_4$, $Q_5$, $Q_6$ and $Q_7$ are each a direct linkage which comprises the step of reducing the corresponding azole-fused peptide of Formula I wherein Y is oxo, n is 1 and $Q_1$, $Q_2$, $Q_3$, $Q_4$, $Q_5$, $Q_6$ and $Q_7$ are each a direct linkage with a boron or aluminum hydride in an inert solvent or solvent mixture.

In a tenth process aspect the invention is the process of preparing an aminoketoamide of Formula XII which comprises the step of condensing the corresponding amino acid of Formula X with the corresponding aminoketone having the structural formula $$H_2N\text{—}CH_2\text{—}CO\text{—}R_4 \quad \text{Formula XVI}$$

by a peptide forming method, concomitantly protecting and deprotecting any free amino or hydroxy, wherein $R_2$, $R_3$, $R_4$ and * are the same as defined for Formula I.

DETAILED DESCRIPTION OF THE INVENTION INCLUSIVE OF THE PREFERRED EMBODIMENTS

Preparation of the compounds
Definitions

The azole-fused peptides of Formula I wherein $Q_1$, $Q_2$, $Q_3$, $Q_4$, $Q_5$, $Q_6$ and $Q_7$ are each a direct linkage can be viewed as dipeptides whose N-terminal amino acid side chain is $R_3$ and whose N-terminal amino acid carbonyl oxygen atom is replaced by X, which forms a bridge (fusion) with the β-carbon atom of the C-terminal amino acid whose β-carbon atom substituent is $R_4$. The thus fused dipeptide is an oxazole when X is oxa, a thiazole when X is thia or an imidazole when X is imido. Its C-terminal carbonyl (Y is oxo, n is 1) can be reduced (Y is two separately bonded hydrogen atoms, n is 1) or eliminated (n is 0).

When $R_2$ taken alone is a hydrogen atom and $R_3$ taken alone is 1-methylethyl, 2-methylpropyl, 4-aminobutyl, 4-hydroxyphenyl, phenylmethyl, pyridylmethyl or (1H-indol-3-yl)methyl, the corresponding amino acid moiety is valyl, leucyl, lysyl, tyrosyl, phenylalanyl, β-pyridylalanyl or tryptophyl, respectively, has the L- or D-configuration or a mixture thereof depending on the configuration of the moiety before azole formation and on the method of azole formation, and is abbreviated herein as Val, Leu, Lys, Tyr, Phe, Bpa or Trp when * is L or val, leu, lys, tyr, phe, bpa or trp when * is D, respectively. When $R_2$ taken together with N, CH and $R_3$ is (2,3,4,9-tetrahydro-1H-pyrido[3,4-b]indol-2,3-diyl), the corresponding amino acid moiety is tryptophyl having a methylene bridge between the 2-position of the indole nucleus and the amino acid nitrogen atom and is abbreviated herein as Tpi when * is L or tpi when * is D. When $Q_3$ is R-(2,3,4,9)-tetrahydro-1H-pyrido[3,4-b]indol-2-yl-3-carbonyl it is abbreviated as tpi.

When $R_4$ is ethyl, propyl, 1-methylethyl, methylthiomethyl, ethylthiomethyl phenyl, 4-hydroxyphenyl, pyridyl or 1H-indol-3-yl the corresponding amino acid moiety is norvalyl, norleucyl, leucyl, methionyl, ethionyl, phenylalanyl, tyrosyl, β-pyridylalanyl or tryptophyl, respectively, and is abbreviated herein as Nva, Nle, Leu, Met, Eth, Phe, Tyr, Bpa or Trp, respectively. These abbreviations, which represent the L-configurations of the amino acid moieties, are used to describe the C-terminal part of the azole-fused dipeptides even though the α-carbon atoms thereof are achiral in their azole forms and no longer actually have either the L- or the D-configuration.

Accordingly the azole-fused dipeptide moiety is abbreviated as a traditional dipeptide moiety with an added bridge representing X of Formula I. When the C-terminal carbonyl is reduced, the further abbreviation ($H_2$) is used, for example, Leu($H_2$). When the C-terminal carbonyl is eliminated, the further abbreviation (des-CO) is used, for example, Phe(des-CO). Table I shows the abbreviations for the fifteen azole-fused dipeptide moieties illustrated in the examples.

TABLE I

Azole-Fused Dipeptide Moiety Abbreviations

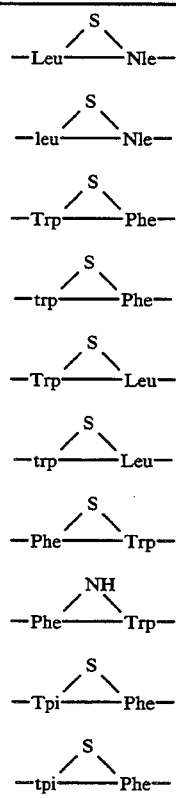

TABLE I-continued

Azole-Fused Dipeptide Moiety Abbreviations

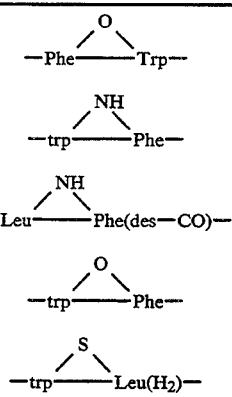

The only variables of Formula I for which abbreviations are used below and not already given above are L-prolyl, N-methyl-L-phenylalanyl, (phenylmethoxy)-carbonyl and (1,1-dimethylethoxy)carbonyl, which are abbreviated below as Pro, MePhe, Z and Boc, respectively.

The thioamino acid moiety of Formula II is abbreviated as, for example, Leu(S) when $R'_3$ is 2-methylpropyl and * is L. Similarly, the aminothioamide of Formula XIII is abbreviated, for example, as Z-Leu(S)-$NH_2$ when $R_2$ is hydrogen, $R_3$ is 2-methylpropyl and * is L (Z represents (phenylmethoxy) carbonyl).

Preparative Methods

The first and fourth through seventh process aspects of the invention pertain to formation of the azole nucleus. The second and third process aspects pertain to preparation of intermediates useful in forming the azole nucleus. The eighth process aspect pertains to completion of the peptide chain after the azole nucleus is formed. The ninth process aspect pertains to preparation of the azole-fused peptides of Formula I wherein n is 1 and Y is two separately bonded hydrogen atoms. The tenth process aspect pertains to preparation of intermediates useful in preparing the azole-fused peptides of Formula I wherein n is 0 and $Q_5$, $Q_6$ and $Q_7$ are each a direct linkage and thus wherein $R_5$ is a hydrogen atom.

In the first and second process aspects of the invention the peptides of Formula II and Formula IV are generally known and are prepared by the peptide forming methods described below. The inert solvent or solvent mixture can be any solvent or mixture thereof which does not interfere with the reaction including water, alcohols, for example, methanol or ethanol, acids, for example, acetic acid, nitriles, for example, acetonitrile, amides, for example, dimethylformamide, and ethers, for example, tetrahydrofuran. In the first process aspect tetrahydrofuran alone is preferred. In the second process aspect, which requires the presence of water, a mixture of tetrahydrofuran and water is preferred. The oxidation is carried out at a temperature in the range of 0°–100° C.

In the third process aspect of the invention the acid chlorides of Formula VI, the iminoesters of Formula VII and the amino acids of Formula X are generally known and are commercially available or are prepared by known methods. In the first step thereof the alkali metal of the alkali metal alkoxide can be lithium, sodium or potassium and the alkoxide can be any alkoxide of one to four carbon atoms. Potassium 1,1-dimethylethoxide is preferred. The inert solvent or solvent mixture can be any solvent or mixture thereof which does not interfere with the reaction including especially ethers. Tetrahydrofuran is preferred. In the second step the mineral acid can be any mineral acid which effects hydrolysis without also causing oxidation or reduction. Hydrochloric acid and sulfuric acid are preferred. The temperature range for both steps is −100°to 50° C. The preferred temperature for the first step is about −80° C. The third step is carried out by any of the peptide forming methods described below.

In the fourth process aspect of the invention the compounds of Formula XI are prepared by the method of the second process aspect of the invention and the compounds of Formula XII are prepared by the tenth process aspect of the invention. The process is carried out at a temperature in the range of 0°–100° C.

In the fifth process aspect of the invention the aminothioamides of Formula XIII, the ketochloroesters of Formula XIV and the epoxychloroesters of Formula XV are generally known and are prepared by known methods. The inert solvent or solvent mixture can be any solvent or solvent mixture which does not interfere with the reaction including alcohols, for example, methanol or ethanol, acids, for example, acetic acid, nitriles, for example, acetonitrile, amides, for examples, dimethylformamide, and ethers, for example, tetrahydrofuran. Ethanol is preferred. The condensation is carried out at a temperature in the range of 50°–50° C.

In the sixth process aspect of the invention the amide thionating reagent is any reagent capable of converting oxo of a carboxamide to thio, for example, phosphorous pentasulfide or 2,4-bis(4-methoxyphenyl)-1,3-dithia-2,4-diphosphetane-2,4-disulfide (Lawesson's reagent). The latter is preferred. The inert solvent or solvent mixture can be any solvent or solvent mixture which does not interfere with the reaction including aromatic hydrocarbons, for example, toluene, alcohols, for example, methanol or ethanol, nitriles, for example, acetonitrile and ethers, for example, tetrahydrofuran. Tetrahydrofuran is preferred. The thionation is carried out at a temperature in the range of 50°–150° C.

In the seventh process aspect of the invention the anion of the ammonium salt can be any anion which does not interfere with the reaction including chloride, sulfate and acetate. The preferred ammonium salt is ammonium acetate. The inert solvent or solvent mixture can be any solvent or solvent mixture which does not interfere with the reaction including aromatic hydrocarbons, for example, toluene, alcohols, for example, methanol or ethanol, nitriles, for example, acetonitrile, amides, for example, dimethylformamide, and ethers, for example, tetrahydrofuran. The cyclization is carried out at a temperature in the range of 50°–150° C.

The eighth and tenth process aspects of the invention and the third step of the third process aspect of the invention are peptide forming methods whose protection, activation, condensation and deprotection steps are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and peptide intermediates can be formed and used with or without being isolated and include the acyl halides and pseudohalides, especially the acyl azides; the anhydrides, especially the mixed anhydrides and most especially the mixed anhydride with diphenylphosphinyl chloride or isobutyl chloroformate; derivatives formed by addition reactions, especially using dicyclohexylcarbodiimide; displaceable acyl derivatives of heterocyclic nitrogen; ring-openable activated heterocyclic systems; acylphosphonium derivates; and activated esters, especially 1-hydroxybenzotriazole (HOBt), N-hydroxysuccinimide (HOSu) and pentafluorophenyl (PFP) esters. In carrying out solid phase (Merrifield) peptide synthesis the preferred carboxyl-activated amino acid derivative is the symmetrical anhydride.

It is necessary that the N-terminal α-amino group be protected during the peptide forming steps. The preferred α-amino protecting groups are (phenylmethoxy)carbonyl (Z), which can be removed by catalytic hydrogenation using palladium as catalyst or by hydrogen bromide in acetic acid or liquid hydrogen fluoride and anisole, and (1,1-dimethylethoxy)carbonyl (Boc), which can be removed by acidic cleavage, for example, with hydrogen chloride in a suitable solvent or trifluoroacetic acid with or without a solvent or liquid hydrogen fluoride and anisole. A protecting group which can be removed in the presence of (phenylmethoxy)carbonyl or (1,1 -dimethylethoxy)carbonyl under basic conditions, for example piperidine in dimethylformamide, is 9-fluorenylmethoxycarbonyl (Fmoc).

The C-terminal carboxyl group must also be protected during the peptide forming steps. That of the compounds of Formula I wherein $R_5$ is amino or substituted amino is protected as the amide, which is a required structural feature thereof and is therefore not removed, except in solid phase peptide synthesis, wherein the C-terminal carboxyl group is protected as a resin-bonded benzylic ester (Bzl-resin) and converted into the amide by ammonolysis in the penultimate step. The C-terminal carboxyl groups of the intermediate amino acids and peptides can be protected as the carboxylate salt, the t-butyl (tBu) ester, which can be removed by acidic cleavage, for example, with hydrogen chloride or trifluoroacetic acid in a suitable solvent, the benzyl (Bzl) ester, which can be removed by catalytic hydrogenation using palladium as catalyst or the methyl ester, which can be removed by alkaline hydrolysis.

The intermediate amino acids including those of Formula X and peptides and the protected derivatives thereof and the aminoketones of Formula XVI necessary to carry out the peptide forming methods of the invention are generally known and are commercially available or are prepared by known methods.

In the ninth process aspect of the invention the boron or aluminum hydride is any boron or aluminum hydride capable of reducing amide carbonyl to methylene without reducing any other part of the molecule including diborane, diisobutylaluminum hydride and lithium aluminum hydride. The inert solvent or solvent mixture can be any solvent or mixture thereof which does not interfere with the reaction including especially ethers. Tetrahydrofuran is preferred. The reduction is carried out at a temperature in the range of 0°–100° C. The acid addition salts of the azole-fused peptides of Formula I are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The azole-fused peptides of Formula I and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophilization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GC), column chromatography, high pressure liquid chromatography (HPLC), medium pressure liquid chromatography (MPLC), thin layer chromatography (TLC) and/or amino acid analysis.

EXAMPLE 1

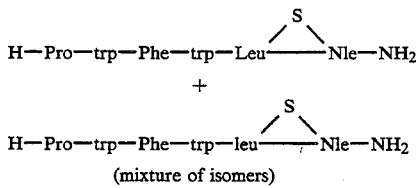

(mixture of isomers)

Thionation of Z-Leu-NH₂ ( 20.0 g.) with phosphorous pentasulfide (3.38 g.) in tetrahydrofuran (250 ml.) at 45° C. overnight, isolation of the crude product (23.9 g.) by ethyl acetate extraction, and purification by HPLC on silica gel using hexane-ethyl acetate (3:1) as eluant followed by crystallization from ethyl acetate-hexane gave Z-Leu(S)-NH₂ in two crops (10.1 g., 2.3 g.; 58% yield; m.r. 77°-79° C.).

Condensation of Z-Leu(S)-NH₂ (7.00 g.) and a mixture of ethyl 3-chloro-2-oxohexanoate and ethyl 2,3-epoxy-3-chlorohexanoate (prepared from butyraldehyde and ethyl dichloroacetate with sodium ethoxide in ethanol-ether; 4.83 g. and 3.2 g. in two increments, the second increment after 4 hr. of reflux) in ethanol ( 100 ml., stripped after 9 hr. of reflux and replaced with an equal amount) under reflux for 10 hr., isolation of the crude product by vacuum stripping and filtration, and purification by HPLC on silica gel using hexane-ethyl acetate (87:13) as eluant gave

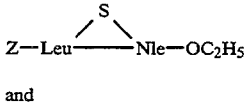

and

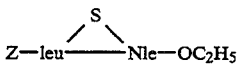

(mixture of isomers) as a pale yellow oil (5.3 g., 51% yield), part (565 mg.) of which crystallized on standing and was triturated with hexane and dried (m.r. 78°-80° C.).

Hydrolysis of

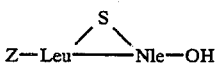

and

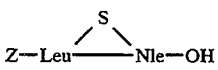

(mixture of isomers, 4.66 g.) with sodium hydroxide (two 444 mg. portions) in dioxane (75 ml.)-water (5 ml.) at room temperature over the weekend and then for 3 hr. after adding the second portion of sodium hydroxide, isolation of the crude product (4.6 g.) by ethyl acetate extraction with acidification, and purification by recrystallization from ethyl acetate gave

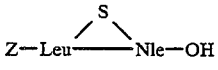

and

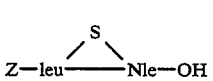

(mixture of isomers) as a white solid (2.92 g., m.r. 104°-106° C., 67% yield)

Condensation of

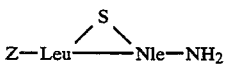

and

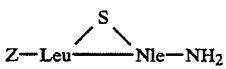

(mixture of isomers, 3.50 g.) and concentrated aqueous ammonia (1.21 ml.) by the mixed anhydride method using diphenylphosphinyl chloride (2.12 g.) and triethylamine (907 mg.) in tetrahydrofuran (40 ml.) for 20 min. at −20° C. and then for 3 hr. at room temperature, isolation of the crude product by ethyl acetate extraction, and purification by HPLC on silica gel using hexane-ethyl acetate (75:25) as eluant and crystallization from ethyl acetate-hexane gave

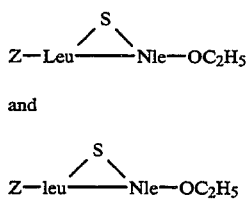

and

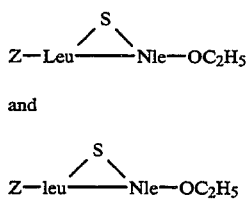

(mixture of isomers; two crops: white solid, 2.3 g., m.r. 95°-97° C. and yellow gum, 0.75 g.; 87% yield).

De-(phenylmethoxy)carbonylation of

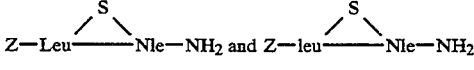

(mixture of isomers 2.46 g.) with hydrogen bromide in acetic acid (37%, 15 ml.) for 0.5 hr. at room temperature, isolation of the product by ethyl acetate extraction, conversion into the hydrochloride salt (1.33 g., 72% yield) and recrystallization from ether-ethanol gave

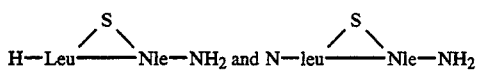

(mixture of isomers) as the monohydrochloride salt monohydrate (m.r. 150°–154° C., [α]$_D^{25}$ −2.6°)

Condensation of Boc -Pro-trp-Phe-OH (part B of example 17 of above-cited U.S. Pat. 4,472,305, 10.97 g.) and H-trp-OCH$_3$ hydrochloride salt (5.09 g.) using dicyclohexylcarbodiimide (4.12 g.), N-hydroxysuccinimide (2.30 g.) and diisopropylethylamine (2.59 g.) in tetrahydrofuran (100 ml.) for 1.5 hr. at 0° C. and then at room temperature overnight, and isolation of the product by ethyl acetate extraction gave Boc-Pro-trp-Phe-trp-OCH$_3$ as a foam (15.1 g., theory, 15.0 g.).

Condensation of Boc-Pro-trp-Phe-trp-OCH$_3$ (14.8 g.) and hydrazine hydrate (10 ml.) in ethanol (150 ml.) at room temperature over the weekend gave Boc-Pro-trp-Phe-trp-NHNH$_2$ as a white solid (11.8 g., 80% yield).

Condensation of Boc-Pro-trp-Phe-trp-NHNH$_2$ (1.73 g.) and

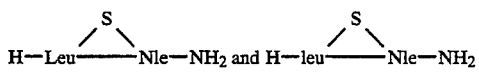

(mixture of isomers) monohydrochloride salt monohydrate (675 mg.) by the acyl azide method using butyl nitrite (0.271 ml.), hydrogen chloride (2.55N in dimethylformamide, 0.906 ml.) and diisopropylethylamine (896 mg.) at 0° C. during mixing of the reactants and in the refrigerator for 20 hr., isolation of the crude product by ethyl acetate extraction, and purification by HPLC on silica gel using ethyl acetate-hexane (95:5) as eluant gave

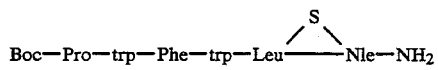

and

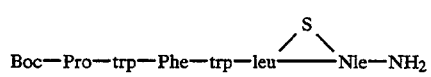

(mixture of isomers, 550 mg., 25% yield).

De-(1,1-dimethylethoxy)carbonylation of

and

(mixture of isomers, 420 mg.) using ethanedithiol (0.9 ml.), dimethylsulfide (10 ml.) and trifluoroacetic acid (9 ml.) for 1.5 hr. at room temperature, purification of the crude product by reverse phase HPLC on octadecylsilated silica gel using methanol-water (4:1) containing ammonium acetate (0.2%) as eluant (two passes) followed by ethyl acetate extraction and lyophilization of the purified product from acetic acid gave

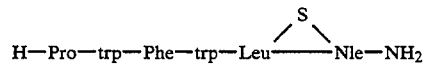

and

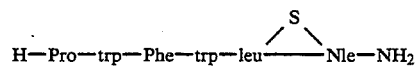

(mixture of isomers) monoacetate salt dihydrate as an amorphous white solid (300 mg., 71% yield).

EXAMPLE 2

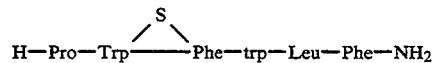

Thionation of Z-trp-NH$_2$ (4.0 g.) with phosphorous pentasulfide (0.844 g.) in tetrahydrofuran (50 ml.) at 45° C. for 3 hr., isolation of the crude product (5.1 g.) by ethyl acetate extraction, and purification by filtration through silica gel (75 g.) with ethyl acetate as eluant followed by HPLC on silica gel using hexane-ethyl acetate (60:40) as eluant gave Z-trp(S)-NH$_2$ as a white foam (3.16 g., 75% yield).

Condensation of Z-trp(S)-NH$_2$ (1.00 g.) and ethyl 3-chloro-2-oxo-3-phenylpropionate (prepared from benzaldehyde and ethyl dichloroacetate with sodium ethoxide in ethanol-ether, 0.68 g.) in ethanol (10 ml.) under reflux for 6 hr., isolation of the crude product by ethyl acetate extraction, and purification by HPLC on silica gel using hexane-ethyl acetate (65:35) as eluant (1.08 g., 73% yield) followed by crystallization from ether-hexane gave

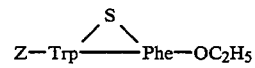

and

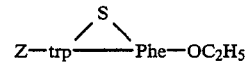

(mixture of isomers) as a pale yellow solid (850 mg., m.r. 105°–108° C.).

Hydrolysis of

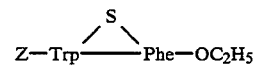

and

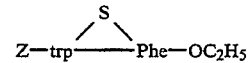

(mixture of isomers, 5.0 g.) with aqueous sodium hydroxide (two 381 mg. portions, first in 2 ml., second in 3 ml. of water) in dioxane (50 ml.) at room temperature for 4 hr. and then overnight after adding the second portion of sodium hydroxide, isolation of the crude product (5.9 g.) by ethyl acetate extraction, and purification by crystallization from ethyl acetate-hexane gave

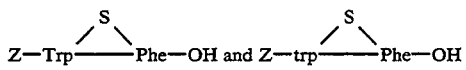

(mixture of isomers) as a white solid (4.2 g., 86yield, m.r. 118°–123° C.).

Condensation of Boc-Leu-OH monohydrate (20.0 g., dehydrated under vacuum) and H-Phe-NH₂ acetate salt (18.0 g.) by the mixed anhydride method using isobutyl chloroformate (10.44 ml.) and triethylamine (two 8.12 g. portions) in tetrahydrofuran (350 ml.) at −20° C. for 45 min. and then at room temperature overnight, isolation of the product by ethyl acetate extraction, and crystallization from hexane gave Boc-Leu-Phe-NH₂ (24.3 g., 80% yield, m.r. 129°–134° C.).

De-(1,1-dimethylethoxy)carbonylation of Boc-Leu-Phe-NH₂ (24.0 g.) was carried out using hydrogen chloride in ethyl acetate (4.4N, 200 ml.) for 2 hr. at room temperature. Upon attempted extraction with ethyl acetate the product unexpectedly entered the saturated aqueous sodium bicarbonate wash solution, which was subjected in its entirety to reverse phase HPLC on octadecylsilated silica gel. The column was washed with water. The product was eluted with methanol and crystallized from ethanol-ether-hexane affording H-Leu-Phe-NH₂as a tan solid (13.0 g., 74% yield, m.r. 127°–131° C.).

Condensation of Z-trp-OH ( 9.76 g.) and H-Leu-Phe-NH₂ (8.0 g.) by the mixed anhydride method using isobutyl chloroformate ( 3.75 ml.) and triethylamine (2.91 g.) in tetrahydrofuran (100 ml.) at −20° C. for 1 hr. and then at room temperature overnight, isolation of the product by ethyl acetate extraction, and crystallization from ethyl acetate gave Z-trp-Leu-Phe-NH₂ (12.5 g., 73% yield, m.r. 195°–198° C.).

De-(phenylmethoxy)carbonylation of Z-trp-Leu-Phe-NH₂ (12.0 g.) by hydrogenation in a Parr shaker with palladium-on-carbon (10%, 1.0 g.) in acetic acid (100 ml.) and purification of the product by crystallization from ethyl acetate, distribution between ethyl acetate and saturated aqueous sodium bicarbonate solution and trituration with isopropyl acetate gave H-trp-Leu-Phe-NH₂ as a solid (7.2 g., 77% yield).

Condensation of

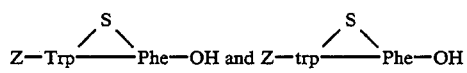

(mixture of isomers, 3.4 g.) and H-trp-Leu-Phe-NH₂ (3.06 g.) by the mixed anhydride method using isobutyl chloroformate (0.86 ml.) and triethylamine (667 mg.) in tetrahydrofuran (60 ml.) at −20° C. for 1 hr. and then at room temperature overnight, isolation of the crude product by ethyl acetate extraction, and purification by filtration through silica gel (100 g.) with ethyl acetate as eluant followed by HPLC on silica gel using ethyl acetate as eluant gave

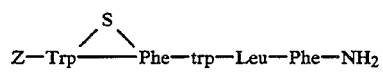

and

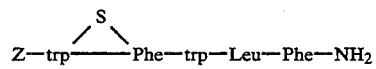

(mixture of isomers, 1.62 g., 26% yield).

De-(phenylmethoxy)carbonylation of

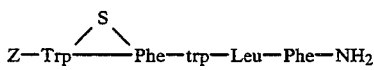

and

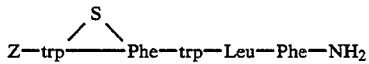

(mixture of isomers, 1.4 g.) with liquid hydrogen fluoride (30 ml.) and anisole (5 ml.) at 0° C. for 0.5 hr. and purification of the crude product (1.11 g.) by column chromatography on silica gel using ethyl acetate-pyridine-acetic acid-water (275: 54: 16: 30) as eluant followed by lyophilization from acetic acid gave

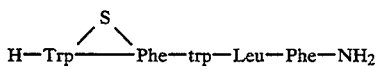

(400 mg.) and

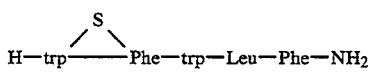

(645 mg.) and a mixture thereof, the mixture thereof as the amorphous white solid diacetate salt monohydrate (140 mg., 84% total yield).

Condensation of Boc-Pro-OSu (145 mg.) and

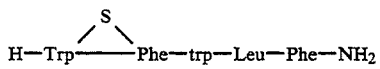

diacetate salt monohydrate (368 mg.) with diisopropylethylamine (54 mg. initially and enough more after 1 hr. to make the pH 6.0) in tetrahydrofuran (10 ml.) at room temperature overnight and purification of the crude product by reverse phase HPLC on octadecyl-silated silica gel using methanol-water (4: 1) as eluant followed by extraction with ethyl acetate gave

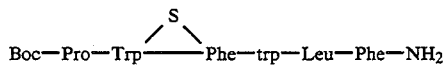

as a white foam (340 mg., 80% yield).

De-(1,1-dimethylethoxy)carbonylation of

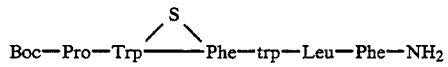

(300 mg.) using trifluoroacetic acid-water (70:30, 30 ml.) for 30 min. at room temperature, isolation of the product by ethyl acetate extraction, and lyophilization from acetic acid gave

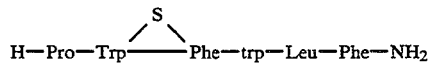

monoacetate salt sesquihydrate as an amorphous white solid (247 mg., 83% yield).

EXAMPLE 3

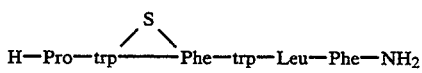

A. Condensation of Boc-Pro-OSu (250 mg.) and

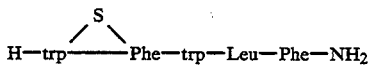

(example 2, 640 mg.) with diisopropylethylamine (95 mg. initially and enough more after 1 hr. to make the pH 6.0) in tetrahydrofuran (10 ml.) at room temperature overnight and purification of the crude product by reverse phase HPLC on silica gel using methanol-water (4:1) as eluant followed by ethyl acetate extraction gave

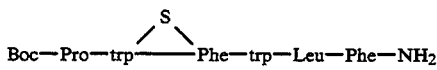

as a white foam (540 mg., 70% yield).

De-(1,1-dimethylethoxy)carbonylation of

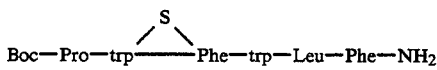

(494 mg.) using trifluoroacetic acid-water (70:30, 50 ml.) for 30 min. at room temperature, isolation of the product by ethyl acetate extraction, and lyophilization from acetic acid gave

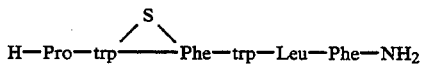

monoacetate salt sesquihydrate as an amorphous off-white solid (407 mg., 84% yield).

B. Methyl 2-amino-3-oxo-3-phenylpropionate ($NH_2$ $CH(COC_6H_5)$—$COOCH_3$) hydrochloride salt was prepared by the method of Suzuki et al. (Syn. Comm., vol. 2, no. 4, pp. 237-242, 1972) in 77% yield in three crops having m.r. 165°-172° C. , 168°-175° C. and 155°-172° C. and by the following new method.

Acylation of $C_6H_5$=CH=N—$CH_2$—$COOCH_3$ (53.1 g., prepared from $C_6H_5$—CHO and $NH_2$—$CH_2$—$COOCH_3$ hydrochloride salt with triethylamine and anhydrous magnesium sulfate in dichloromethane at room temperature in 93% yield) with $C_6H_5$—COCl (42.18 g.) was carried out at −78° C. under an argon atmosphere with stirring by adding a solution of the $C_6H_5CH$=N—$CH_2$—$COOCH_3$ in tetrahydrofuran (150 ml.) to a solution of $(CH_3)_3COK$ (33.6 g.) in tetrahydrofuran (250 ml.) during 20 min., stirring the red solution for 0.5 hr., adding it during 2.5 hr. through a double-tip needle to a solution of the $C_6H_5$—COCl in tetrahydrofuran (150 ml.), and stirring the reaction mixture for 1 hr. to form $C_6H_5$—CH=N—$CH(COC_6H_5)$—$COOCH_3$, hydrolysis of which was carried out by adding hydrochloric acid (3N, 300 ml.) with continued stirring and cooling (the temperature rose to −10° C.) and then discontinuing cooling for 2.5 hr. (the temperature rose to 10° C.). The reaction mixture was reduced in volume by one half and extracted twice with ether. The aqueous layer was concentrated and the residue was stripped three times from methanol with filtering. Crystallization of the crude product (55 g.) from methanol-ether gave $H_2N$—$CH(COC_6H_5)$—$COOCH_3$ hydrochloride salt in two crops (4.68 g., 24.6 g.) and the remainder as a foam (20.6 g., 72% yield).

By a similar method $H_2N$—$CH(COC_6H_5)$—$COOCH_3$ hydrochloride salt was prepared in 86% yield from equimolar amounts of $(C_6H_5)_2C$=N—$CH_2$—$COOCH_3$ (prepared from $(C_6H_5)_2C$=NH and $NH_2$—$CH_2$—$COOCH_3$ hydrochloride salt in dichloromethane at room temperature in 100% yield), $C_6H_5$—COCl and $(CH_3)_3COK$.

Condensation of Z-trp-OH (35.5 g.) and $NH_2$—$CH(COC_6H_5)$—$COOCH_3$ hydrochloride salt (24.0 g.) by the mixed anhydride method using isobutyl chloroformate (13.7 ml.) and triethylamine (two 10.63 g. portions) in tetrahydrofuran (500 ml.) at −25±5° C. during the addition times and for 15 min. thereafter and then at room temperature overnight, isolation of the product by ethyl acetate extraction, and purification by a combination of crystallization from dichloromethane and HPLC on silica gel using hexane-ethyl acetate as eluant gave Z-trp-NH—$CH(COC_6H_5)$—$COOCH_3$ as a crystalline solid in three crops (23.9 g., m.r. 183°-190° C.; 5.4 g., m.r. 191°-197° C; 3.8 g., m.r. 193°-197° C.; 61.% yield).

Cyclization of Z-trp-NH—$CH(COC_6H_5)$—$COOCH_3$ (3.0 g.) with Lawesson's reagent (2.42 g. initially and an equal amount after 4 hr. of reflux) in tetrahydrofuran (30 ml.) for 6 hr. under reflux in a nitrogen atmosphere and purification of the product by column chromatography on silica gel using hexane-ethyl acetate (1:1) as eluant followed by recrystallization from methanol-hexane gave

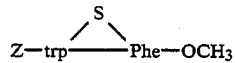

(1.97 g., 66% yield, $[\alpha]_D^{25}$ +13.4° in dimethylformamide at c=1).

Hydrolysis of

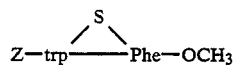

(1.75 g.) using aqueous sodium hydroxide (1.0N, 3.5 ml.) in dioxane (20 ml.) at room temperature for 3 hr. and isolation of the product by ethyl acetate extraction gave

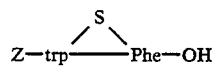

(1.33 g., 78% yield, m.r. 85°-95° C., $[\alpha]_D^{25}$ +15.3°)

Condensation of

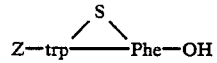

(1.20 g.) and H-trp-Leu-Phe-$NH_2$ (example 2, 1.12 g.) using dicyclohexylcarbodiimide (500 mg.) and N-hydroxysuccinimide (277 mg.) and purification of the product by column chromatography on silica gel using ethyl acetate as eluant gave

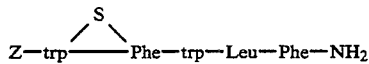

(1.65 g., 73% yield).

Repetition of the last three steps of example 2 starting with

(1.0 g.) gave

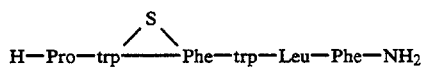

as the diacetate salt monohydrate (550 mg., 50% overall yield). In the next to last step normal phase instead of reverse phase HPLC was used and the eluant was ethyl acetate-isopropyl alcohol (98:2) instead of methanol-water (4:1). The product of the second from last step was identified by TLC comparison with a corresponding product made by the method of example 2. The final product (except as to extent of salt formation with acetic acid and hydration) was identified by IR and NMR spectral comparison with the final product of part A of this example.

EXAMPLE 4

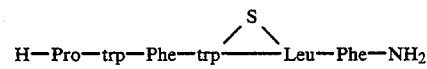

Condensation of Z-trp(S)-NH$_2$ (example 2, 7.0 g.) and ethyl 3-chloro-4-methyl-2-oxopropionate (prepared from 2-methylpropionaldehyde and ethyl dichloroacetate with sodium ethoxide in ethanol-ether, 5.78 g. and an equal amount after 14 hr. of reflux) in ethanol (70 ml.) under reflux for 22 hr., isolation of the crude product by ethyl acetate extraction, and purification by HPLC on silica gel using hexane-ethyl acetate (65:35) as eluant followed by recrystallization from ethyl acetate-hexane gave

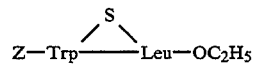

and

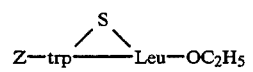

(mixture of isomers) in two crops (2.93 g., m.r. 145°–148° C.; 1.14 g.; 42% yield).

Hydrolysis of

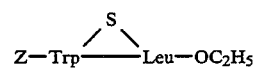

and

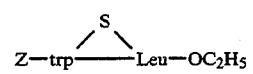

(mixture of isomers, 2.2 g.) with aqueous sodium hydroxide (400 mg. in 4 ml. of water) in dioxane (20 ml.) at room temperature overnight, isolation of the crude product (2.5 g.) by extraction with ether, and purification by crystallization from ether-hexane gave

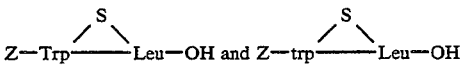

(mixture of isomers) as a white solid (1.68 g., 81% yield, m.r. 113°–15° C.).

Condensation of

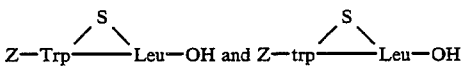

(mixture of isomers, 1.1 g.) and H-Phe-NH$_2$ (0.532 g.) by the mixed anhydride method using diphenylphosphinyl chloride (561 mg.) and diisopropylethylamine (613 mg.) at −20° C. for 1 hr. and then at room temperature for 3 hr., isolation of the crude product (1.5 g.) by ethyl acetate extraction, and purification by reverse phase HPLC on octadecylsilated silica gel using methanol-water (77:23) as eluant gave

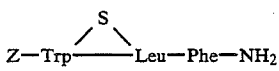

and

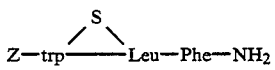

(mixture of isomers) as a crystalline solid (683 mg., 47% yield, m.r. 108°–118° C.).

De-(phenylmethoxy)carbonylation of

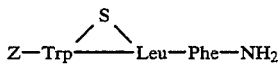

and

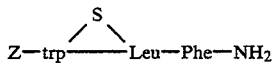

(mixture of isomers, 670 mg.) with liquid hydrogen fluoride (30 ml.) and anisole (4.5 ml.) at 0° C. for 0.5 hr., isolation of the crude product by ethyl acetate extraction, and purification by column chromatography on silica gel using ethyl acetate-pyridine-acetic acid-water (300:54:16:30) as eluant followed by lyophilization from acetic acid gave

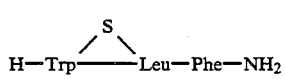

(98 mg.) and

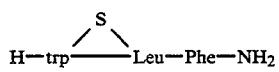

(406 mg.) as what was assumed to be the monoacetate salt (86% yield).

Condensation of Boc-Pro-trp-Phe-OH (part B of example 17 of above-cited U.S. Pat. 4,472,305, 483 mg.) and

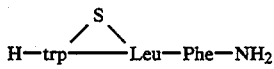

(assumed to be the monoacetate salt, 393 mg.) using dicyclohexylcarbodiimide (181 mg.), N-hydroxy-succinimide (101 mg.) and diisopropylethylamine (114 mg.) in tetrahydrofuran (10 ml.) for 0.5 hr. at −20° C. and then for 1 hr. at room temperature, adjustment of the pH to 7.0 with diisopropylethylamine, and purification of the crude product by reverse phase HPLC on octadecylsilated silica gel using methanol-water (85:15) as eluant gave

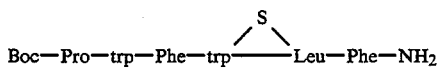

as a solid (539 mg., 73% yield).

De-(1,1-dimethylethoxy)carbonylation of

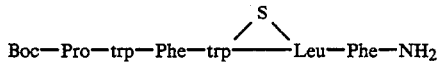

(524 mg.) using trifluoroacetic acid-water (70:30, 50 ml.) for 0.5 hr. at room temperature, isolation of the product by ethyl acetate extraction, and lyophilization from acetic acid gave

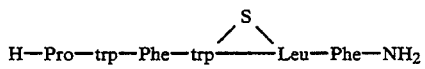

monoacetate salt dihydrate as an amorphous solid (469 mg., 90% yield).

EXAMPLE 5

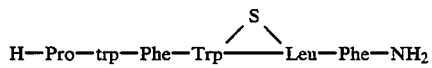

Condensation of Boc-Pro-trp-Phe-OH (part B of Example 17 of above-cited U.S. Pat. No. 4,472,305, 110 mg.) and

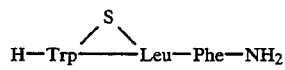

(example 4, assumed to be the monoacetate salt, 90.0 mg.) using dicyclohexylcarbodiimide (41.2 mg.). N-hydroxysuccinimide (23 mg.) and diisopropylethylamine (26 mg.) in tetrahydrofuran (5 ml.) for 0.5 hr. at −20° C. and then for 1 hr. at room temperature, adjustment of the pH to 7.0 with diisopropylethylamine, and purification of the crude product by reverse phase HPLC on octadecylsilated silica gel using methanol-water (85:15) as eluant gave

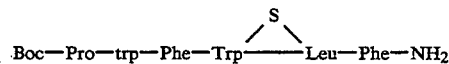

as a solid (132 mg., 78% yield).

De-(1,1-dimethylethoxy) carbonylation of

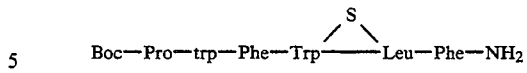

(129 mg.) using trifluoroacetic acid-water (70:30, 15 ml.) for 0.5 hr. at room temperature, isolation of the product by ethyl acetate extraction, and lyophilization from acetic acid gave

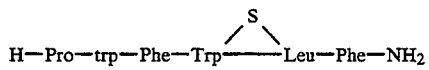

monoacetate salt monohydrate as an amorphous solid (107 mg., 79% yield).

EXAMPLE 6

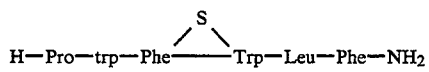

Condensation of Z-Phe-OH (15.0 g.) and H-Trp-OCH$_3$ (12.8 g.) by the mixed anhydride method using isobutyl chloroformate (6.52 ml.) and triethylamine (10.1 g.) in tetrahydrofuran for a few minutes at −20° C. and then for about 1 hr. at room temperature, isolation of the crude product by ethyl acetate extraction, and purification by crystallization from ether-hexane gave Z-Phe-Trp-OCH$_3$(21.5 g., 8670 yield).

Thionation of Z-Phe -Trp-OCH$_3$( 8.0 g.) with phosphorus pentasulfide (4.0 g.) in tetrahydrofuran (75 ml.) and purification of the crude product by reverse phase HPLC on octadecylsilated silica gel using methanol-water (4:1) as eluant and extraction with ethyl acetate gave Z-Phe(S)-Trp-OCH$_3$ (5.8 g., 70% yield).

Oxidation and cyclization of Z-Phe(S) -Trp-OCH$_3$ (3.9 g.) with 2,3-dichloro-5,6-dicyanoquinone (3.43 g.) in tetrahydrofuran (40 ml.) under reflux for 2 hr., isolation of the crude product by ethyl acetate extraction, and purification by filtration through silica gel with ethyl acetate followed by HPLC on silica gel using ethyl acetate-hexane (45:55) as eluant gave

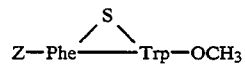

as a foam (1.95 g., 50% yield).

Hydrolysis of

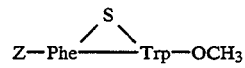

(1.8 g.) with sodium hydroxide (200 mg. initially and 70 mg. more after 3 hr.) in dioxane (10 ml.)-water (2 ml.) at room temperature for 6 hr., isolation of the crude product by acidification with citric acid and ethyl acetate extraction, and purification by crystallization from ethyl acetate-ether-hexane and recrystallization from methanol-ether-hexane gave

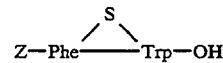

as a yellow solid (1.0 g., 57% yield, m.r. 88°–100° C.).

Condensation of

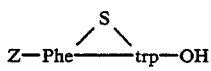

(800 mg.) and H-Leu-Phe-NH$_2$ (example 2, 446 mg.) by the mixed anhydride method using diphenylphosphinyl chloride (381 mg.) and triethylamine (163 mg.) in tetrahydrofuran (10 ml.) for 1 hr. at −20° C. and then for 3 hr. at room temperature, isolation of the crude product (1.3 g.) by ethyl acetate extraction, and purification by HPLC on silica gel using ethyl acetate as eluant followed by crystallization from ethyl acetate-ether-hexane gave

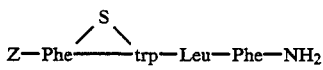

as a yellow solid (790 mg. plus 120 mg. from the mother liquor, 75% yield, m.r. 203°–206° C.).

De-(phenylmethoxy)carbonylation of

(750 mg.) with liquid hydrogen fluoride (20 ml.) and anisole (5 ml.) at 0° C. for 0.5 hr. and purification of the crude product by reverse phase HPLC on octadecylsilated silica gel using methanol-water (80:20) containing ammonium acetate (0.2%) as eluant followed by ethyl acetate extraction gave

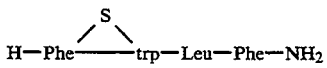

as a yellow foam (589 mg., 95% yield), part (150 mg.) of which was lyophilized from acetic acid and then passed through an ion exchange resin in the phosphate form and lyophilized from water to give the phosphate (1:1) salt hemiacetate.

Condensation of Boc-Pro-trp-OH (part B of example 17 of above-cited U.S. Pat. No. 4,472,305, 274 mg.) and

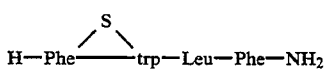

(425 mg.) using dicyclohexylcarbodiimide (141 mg.) and N-hydroxysuccinimide (78 mg.) in tetrahydrofuran (10 ml.) for 1 hr. at 0° C. and then at room temperature overnight and purification of the crude product by reverse phase HPLC on octadecylsilated silica gel using methanol-water (80:20) as eluant followed by extraction with ethyl acetate gave

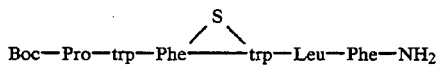

(592 mg., 86% yield).

De-(1,1-dimethylethoxy)carbonylation of

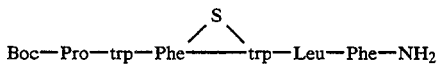

(567 mg.) using trifluoroacetic acid-water (70:30, 20 ml.) for 1 hr. at room temperature, isolation of the product by ethyl acetate extraction, conversion into the phosphate salt by ion exchange chromatography (twice), and lyophilization (twice) from acetic acid gave

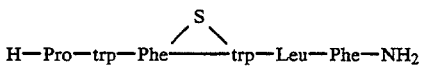

phosphate (2:1) salt monoacetate dihydrate as an amorphous white solid (255 mg., 43% yield).

EXAMPLE 7

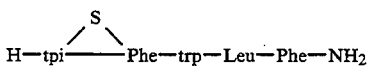

De-(phenylmethoxy)carbonylation of

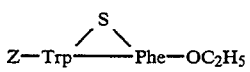

and

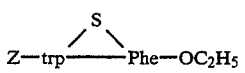

(mixture of isomers, example 2, 9.0 g.) with liquid hydrogen fluoride (40 ml.) and anisole (30 ml.) at 0° C. for 0.5 hr., isolation of the product by first washing the crude hydrofluoride salt with ether-hexane and then freeing the base with aqueous sodium bicarbonate and extracting it into ether, and purification by crystallization from ether gave

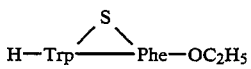

and

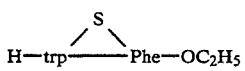

(mixture of isomers) as a white solid (5.45 g., 84% yield, m.r. 118°–121° C.).

Condensation of

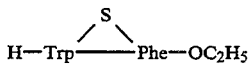

and

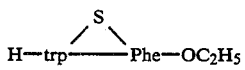

(mixture of isomers, 2.0 g.) with formaldehyde (37%, 430 mg.) in acetic acid (50 ml.) at room temperature and isolation of the product by lyophilization gave

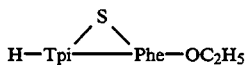

and

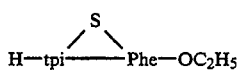

(mixture of isomers).

Hydrolysis of the entire product of the foregoing step with aqueous sodium hydroxide (10%, 6 ml.) in dioxane (10 ml.) for 1.5 hr. at room temperature and isolation of part of the product as the inner salt by addition of more dioxane (10 ml.) and more water (20 ml.) and adjustment of the pH to 8.0 and the remainder of the product as the monoacetate salt by acidification with acetic acid gave

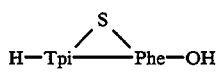

and

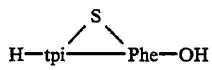

(mixture of isomers; 943 mg. of inner salt, m.p. 210° C. with decomposition; 1.03 g. of monoacetate salt, m.p. 187° C. with decomposition; 92% yield).

Condensation (two runs) of

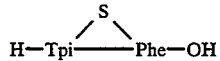

and

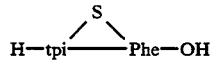

(mixture of isomers, 31.4 mg., 400 mg.) and H-trp-Leu-Phe-NH₂ (example 2, 77.5 mg., 556 mg.) using dicyclohexylcarbodiimide (17.2 mg., 220 mg.) and N-hydroxysuccinimide (9.6 mg., 123 mg.) in tetrahydrofuran (1 ml. 10 ml.) at 0° C. for 0.5 hr. and then at room temperature (overnight, 6 hr.), combination of the crude products, and purification by column chromatography on silica gel first with ethyl acetate-pyridine-acetic acid-water (900:54:16:30) as eluant to give

and

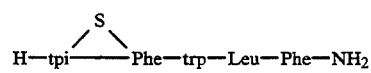

as a mixture of isomers (350 mg., 37% yield) and then with ethyl acetate-pyridine-acetic acid-water (1500:54:16:30) as eluant gave isomer A (75 mg.) and isomer B (125 mg.). Lyophilization of isomer A from acetic acid followed by conversion into the phosphate salt by ion exchange chromatography followed by lyophilization from water-acetic acid (95:5) gave

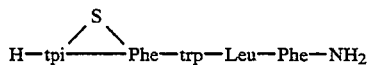

phosphate (1:1) salt as an amorphous pale yellow solid (19 mg.).

EXAMPLE 8

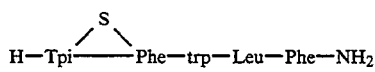

Conversion of isomer B from example 7 into the methanesulfonate salt with aqueous methanesulfonic acid (0.1145 N., 1.27 ml.), attempted lyophilization from water (100 ml., the salt was insoluble), and lyophilization from acetic acid gave

monomethane-sulfonate salt as an amorphous pale yellow solid (71 mg.).

EXAMPLE 9.

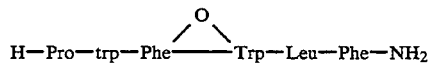

Oxidation of Z-Phe-Trp-OCH₃ and Z-Phe-trp-OCH₃ (mixture of isomers, method prepared by the of example 6, (20.0 g.) with 2,3-dichloro-5,6-dicyanoquinone (18.16 g.) in tetrahydrofuran (200 ml.) for 20 min. at 0° C. 1 hr. at room temperature and 2 hr. under reflux, isolation of the crude product by ethyl acetate extraction, and purification by HPLC, first by normal phase on silica gel using ethyl acetate-hexane (40:60) as eluant, then by reverse phase octadecylsilated silica gel using methanol-water (3:1) as eluant, and finally again by normal phase on silica gel again using ethyl acetate-hexane (40:60) as eluant gave

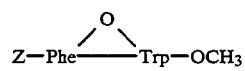

as a brown solid (1.8 g., 9% yield), m.r. 185°–188° C.).

Condensation of

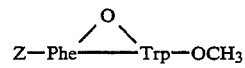

(1.5 g.) and hydrazine hydrate (6 ml.) in methanol-tetrahydrofuran (2:1, 50 ml.) for 8 days at room temperature and isolation of the product by concentrating the reaction mixture to about 25 ml. and adding water (3°–4 ml.) gave

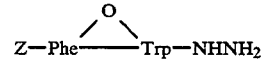

as an off-white solid (1.2 g., 80% yield, m.r. 208°–210° C.) and a second crop as a yellow solid.

Condensation of

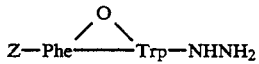

(1.25 g.) and H-Leu-Phe-NH₂ (example 2, 832 mg.) by the acyl azide method using butyl nitrite (0.35 ml.), hydrogen chloride in dimethylformamide (2.55 N, 1.18 ml.) and diisopropylethylamine (388 mg.) in dimethylformamide (10 ml.) at 0° C. during mixing of the reactants and in the refrigerator over the weekend, isolation of the crude product by ethyl acetate extraction, and purification by HPLC on silica gel using ethyl acetate as eluant gave

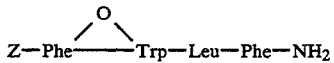

(1.07 g., 57% yield).
De-(phenylmethoxy)carbonylation of

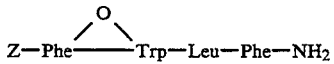

(950 mg.) with liquid hydrogen fluoride (20 ml.) and anisole (5 ml.) at 0° C. for 0.5 hr., isolation of the crude product by ethyl acetate extraction, and crystallization from ethyl acetate-ether gave

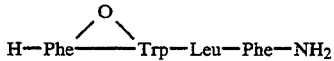

(660 mg., 85% yield, m.r. 188°–193° C.).

Condensation of Boc-Pro-trp-OH (part B of example 17 of above-cited U.S. Pat. No. 4,472,305, 401.5 mg.) and

(606.7 mg.) using dicyclohexylcarbodiimide (206 mg.) and N-hydroxysuccinimide (115 mg.) in tetrahydrofuran for 0.5 hr. at 0° C. and then for 6 hr. at room temperature, isolation of the crude product by ethyl acetate extraction, and purification by HPLC on silica gel ethyl acetate as eluant gave

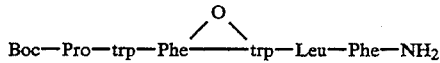

(780 mg., 79% yield).
De-(1,1-dimethylethoxy)carbonylation of

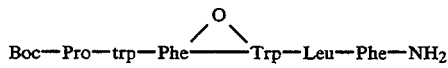

(700 mg.) using trifluoroacetic acid-water (70:30, 25 ml.) for 1.5 hr. at room temperature, isolation of the crystalline product (700 mg., theory, 629 mg.) by stripping and ethyl acetate extraction, lyophilization from acetic acid, conversion of about half of the lyophilizate into the phosphate salt by ion exchange chromatography, and lyophilization from water gave

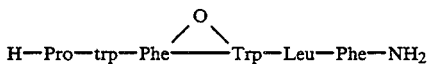

phosphate (1:1) salt monoacetate sesquihydrate as an amorphous off-white solid.

EXAMPLE 10

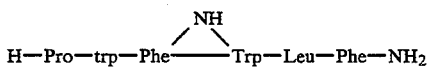

Oxidation of Z-Phe-Trp-OCH₃ (example 6, 11.0 g.) in tetrahydrofuran (50 ml.) with 2,3-dichloro-5,6 dicyanoquinone (10.0 g.) in aqueous tetrahydrofuran (90%, 100 ml.) at room temperature for 3 hr., isolation of the crude product by stripping to water and extracting with ethyl acetate, and purification by filtration through silica gel and HPLC on silica gel using ethyl acetate-hexane (55:45) as eluant gave the β-ketotryptophyl derivative of Z-Phe-Trp-OCH₃ as a yellow foam (4.95 g., 44% yield).

Cyclization of the β-ketotryptophyl derivative of Z-Phe-Trp-OCH₃ (4.8 g.) with ammonium acetate (7.7 g.) in acetic acid (25 ml.) under reflux for 8 hr., isolation of the crude product by stripping the acetic acid and ethyl acetate extraction, and purification by HPLC on silica gel using ethyl acetate-hexane (1:1) as eluant and recrystallization from ethyl acetate hexane gave

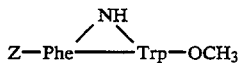

as a white solid (1.6 g., 35% yield, m.r. 157°–160° C.).
Condensation of

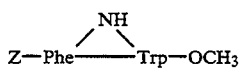

(550 mg.) and hydrazine hydrate (2 ml.) in methanol (10 ml.) at room temperature for 3 days and isolation of the product by ethyl acetate extraction gave

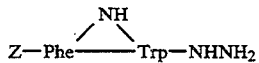

(525 mg., 95% yield).
Condensation of

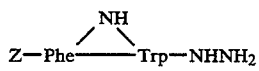

(550 mg.) and H-Leu-Phe-NH₂ (example 2, 294 mg.) by the acylazide method using butyl nitrite (0.136 ml.), hydrogen chloride in dimethylformamide (2.55 N, 0.459 ml.) and diisopropylethylamine (288 mg.) in dimethylformamide (5 ml.) at 0° C. during mixing of the reactants and in the refrigerator overnight, isolation of the crude product by ethyl acetate extraction, and purification by HPLC on silica gel using ethyl acetate-isopropyl alcohol (96:4) as eluant gave

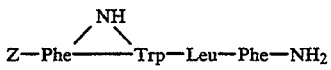

as a yellow foam (110 mg., 14% yield).

De-(phenylmethoxy)carbonylation of

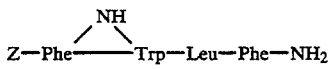

(100 mg.) with liquid hydrogen fluoride (10 ml.) and anisole (2 ml.) at 0° C. for 0.5 hr. and isolation of the product by ethyl acetate extraction (twice) gave

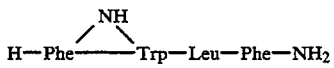

in two parts (34 mg., m.r. 125°-150° C.; 16 mg.; 61% yield).

Condensation of Boc-Pro-trp-OH (part B of example 17 of above-cited U.S. Pat. 4,472,305, 40.1 mg.) and

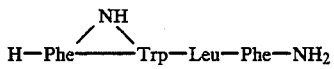

(50.0 mg.) using dicyclohexylcarbodiimide (20.6 mg.) and N-hydroxysuccinimide (11.5 mg.) in dimethylformamide (1 ml.) for 1 hr. at 0° C. and then overnight at room temperature and purification of the product by reverse phase HPLC (two passes) on octadecylsilated silica gel using methanol-water (80:20) as eluant in the first pass and methanol-water (85: 15) as eluant in the second pass gave

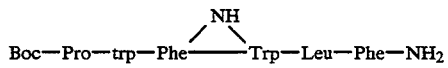

(35 mg., 42% yield).

De-(1,1-dimethylethoxy)carbonylation of

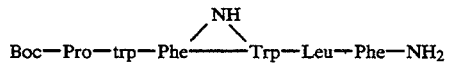

(35 mg.) using trifluoroacetic acid-water (70:30, 5 ml.) for 1.5 hr. at room temperature and isolation of the product by stripping, lyophilization from acetic acid, conversion into the phosphate salt by ion exchange chromatography and lyophilization from water gave

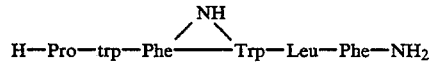

phosphate (1: 1) salt as an amorphous white solid (22 mg., 63% yield).

EXAMPLE 11

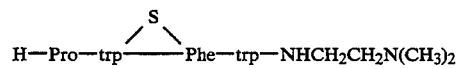

Condensation of

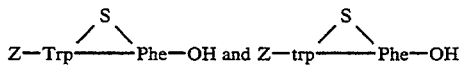

(example 2, mixture of isomers, 24.0 g.) and H-trp-OCH$_3$ hydrochloride salt (12.74 g.) using dicyclohexylcarbodiimide (10.3 g.), N-hydroxysuccinimide (5.75 g.) and diisopropylethylamine (6.46 g.) in tetrahydrofuran (200 ml.) for 0.5 hr. at 0° C. (the pH was then adjusted to 7.0) and then for 3 hr. at room temperature, isolation of the crude product by ethyl acetate extraction, and purification by filtration through silica gel with ethyl acetate-hexane (3:1) followed by HPLC on silica gel using ethyl acetate-hexane (1:1) as eluant gave

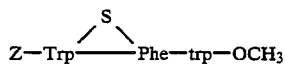

and

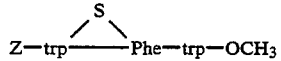

(mixture of isomers) as a foam (25.7 g., 76% yield).

Hydrolysis of

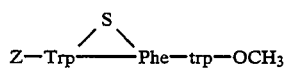

and

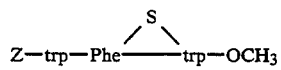

(mixture of isomers, 19.0 g.) with aqueous sodium hydroxide (1.2 g. in 5 ml. of water initially and an equal amount after 1 hr.) in dioxane (100 ml.) at room temperature overnight, isolation of the crude product (20.4 g., theory 18.62 g.) by ethyl acetate extraction, and purification of part (14.4 g.) of it by reverse phase HPLC on octadecylsilated silica gel using methanol-water (85:15) as eluant followed by lyophilization from acetic acid gave

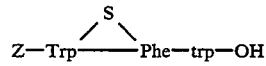

and

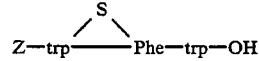

(mixture of isomers) hemiacetate as a foam.

Condensation of

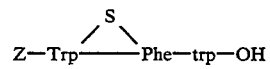

and

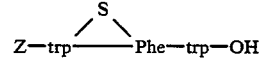

(mixture of isomers, crude product, 6.0 g.) and H$_2$NCH$_2$CH$_2$N(CH$_3$)$_2$ (95% pure, 814 mg.) using dicyclohexylcarbodiimide (1.81 g.) and N-hydroxysuccinimide (1.01 g.) in tetrahydrofuran (60 ml.) for 1 hr. at 0° C. and then at room temperature overnight, isolation of the crude product by ethyl acetate extraction, and purification by reverse phase HPLC on octadecylsilated silica gel using methanol-water (80:20) containing ammonium acetate (0.2%) as eluant gave

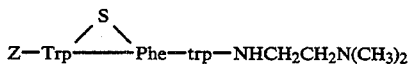

and

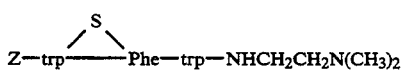

(mixture of isomers) as a foam (5.73 g., 95% yield assuming purity of starting material was 18.62/20.4).

De-(phenylmethoxy)carbonylation of

and

(mixture of isomers, 5.6 g.) with liquid hydrogen fluoride (40 ml.) and anisole (5.0 ml.) at 0° C. for 0.5 hr., isolation of the crude product by ethyl acetate extraction, and purification by column chromatography on silica gel using ethyl acetate-pyridine-acetic acid-water (100:54:16:30) as eluant followed by lyophilization from acetic acid gave.,

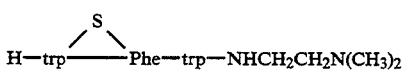

(isomer A, 1.07 g.) and

(isomer B, 1.60 g.) and in addition after further lyophilization from water a mixture thereof (2.44 g., 93% yield assuming that each part of the product was the diacetate salt).

Condensation of Boc-Pro-OSu (219 mg.)and

(assumed to be the diacetate salt, 500 mg.) with triethylamine (137 mg.) in tetrahydrofuran (10 ml.) at room temperature (the pH was adjusted to 7 with triethylamine) overnight, isolation of the crude product by stripping the volatiles, and purification by column chromatography on silica gel using ethyl acetate-pyridine-acetic acid-water (125:54:16:30) as eluant followed by lyophilization from acetic acid gave

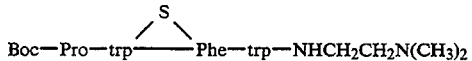

(385 mg., 65% yield assuming that the product was the monoacetate salt).

De-(1,1-dimethylethoxy)carbonylation of

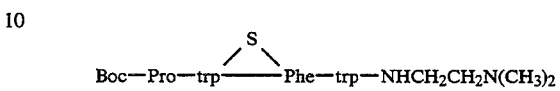

(assumed to be the monoacetate salt, 370 mg.) using trifluoroacetic acid-water (70:30, 50 ml.) for 1 hr. at room temperature and isolation the product by stripping, lyophilization from water, conversion into the phosphate salt by ion exchange chromatography and lyophilization from water gave

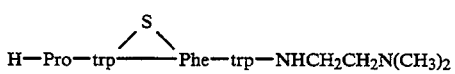

phosphate (1:2) salt hexahydrate as an amorphous off-white solid (296 mg., 69% yield).

EXAMPLE 12

Condensation of Boc-Pro-OSu (328 mg.) and

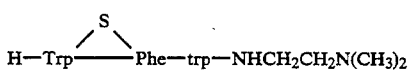

(example 11, assumed to be the diacetate salt, 750 mg.) with triethylamine (205 mg.) in tetrahydrofuran (10 ml.) at room temperature (the pH was adjusted to 7 with triethylamine) overnight, isolation of the crude product by stripping the volatiles, and purification by column chromatography on silica gel using ethyl acetate-pyridine-acetic acid-water (125:54:16:30) as eluant followed by lyophilization from acetic acid gave

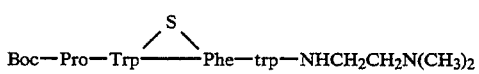

(710 mg., 80% yield assuming that the product was the monoacetate salt).

De-(1,1-dimethylethoxy)carbonylation of

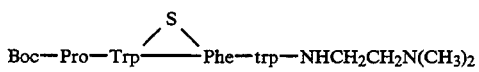

(assumed to be the monoacetate salt, 690 mg.) using trifluoroacetic acid-water (70:30, 50 ml.) for 1 hr. at room temperature and isolation of the product by stripping, lyophilization from water, conversion into the phosphate salt by ion exchange chromatography and lyophilization from water gave

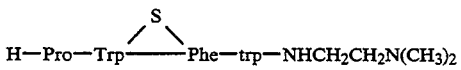

phosphate (1:2) salt pentahydrate as an amorphous light tan solid (416 mg., 53% yield).

EXAMPLE 13

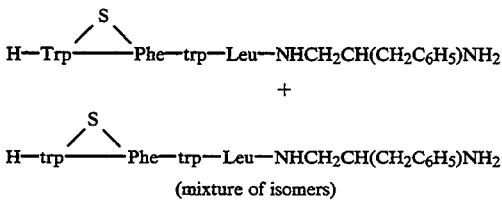

(mixture of isomers)

Condensation of Boc-Leu-OH monohydrate (21.93 g., heated at 40° C. under vacuum to remove water of hydration) and H$_2$NCH$_2$CH(CH$_2$C$_6$H$_5$)NHZ (prepared from Z-Phe-NH$_2$ by diborane reduction, m.r. 71°-73° C., 25.0 g.) by the mixed anhydride method using isobutyl chloroformate (12.01 g.) and triethylamine (8.90 g.) in tetrahydrofuran (300 ml.) briefly at −20° C. and then at room temperature overnight, isolation of the product by ethyl acetate extraction, and crystallization from ethyl acetate-hexane gave Boc-Leu-NHCH$_2$CH-(CH$_2$C$_6$H$_5$)NHZ in two crops (29.4 g., m.r. 162°-164° C.; 7.3 g., m.r. 166°-168° C.; 84% yield).

De-(1,1-dimethylethoxy)carbonylation of Boc-Leu-NHCH$_2$CH(CH$_2$C$_6$H$_5$)NHZ (21.5 g.) using trifluoroacetic acid-water (70:30, 200 ml.) for 1.5 hr. at room temperature, isolation of the crude product by stripping and ethyl acetate extraction, and purification by acidification with acetic acid and trituration with ether and reverse phase HPLC of the residue of the ether washes on octadecylsilated silica gel using methanol-water (70:30) containing ammonium acetate (0.2%) gave H-Leu-NHCH$_2$CH(CH$_2$C$_6$H$_5$)NHZ in two crops (14.8 g. as what was assumed to be the monoacetate salt and 1.88 g. as the free base, 89% yield).

Condensation of Boc-trp-OH (8.66 g.) and H-Leu-NH-CH$_2$CH(CH$_2$C$_6$H$_5$)NHZ (assumed to be the monoacetate salt, 12.5 g.) by the mixed anhydride method using diphenylphosphinyl chloride (6.73 g.) and triethylamine (5.76 g. in two equal portions) at −30° C. for 30 min. and then at room temperature overnight, isolation of the crude product by ethyl acetate extraction, and purification in part (4.1 g.) by crystallization (forming a gel) from isopropyl acetate and in part (5.69 g.) by HPLC on silica gel using ethyl acetate-hexane (70:30) as eluant gave Boc-trp-Leu-NHCH$_2$CH(CH$_2$C$_6$H$_5$)NHZ (50% yield).

De-(1,1-dimethylethoxy)carbonylation of Boc-trp-Leu-NHCH$_2$CH(CH$_2$C$_6$H$_5$)NHZ (9.75 g.) using fluoroacetic acid-water (70:30, 200 ml.) for 2 hr. at room temperature, isolation of the product by stripping and ethyl acetate extraction, and purification by crystallization from ethyl acetate-ether gave H-trp-Leu-NHCH$_2$CH(CH$_2$C$_6$H$_5$)NHZ sesquihydrate as a white solid in two crops (6.29 g., m.r. −170° C.; 310 mg.; 79% yield).

Condensation of

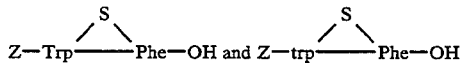

(example 2, mixture of isomers, 1.00 g.)
and H-trp-Leu-NHCH$_2$CH(CH$_2$C$_6$H$_5$)NHZ (1.13 g.) using dicyclohexylcarbodiimide (400 mg.) and N-hydroxysuccinimide (283 mg.) in tetrahydrofuran (25 ml.) at 0° C. and then at room temperature overnight and for 3 hr. more after adding more dicyclohexylcarbodiimide (25 mg.), isolation of the crude product (2.25 g.) by ethyl acetate extraction, and purification by HPLC on silica gel using first hexane-ethyl acetate (1:1) and then ethyl acetate as eluant followed by crystallization from ethyl acetate-hexane gave

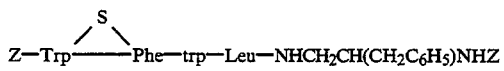

and

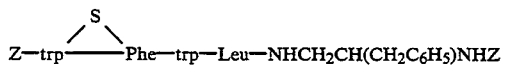

(mixture of isomers, 1.23 g., 59% yield).

De-(phenylmethoxy)carbonylation of

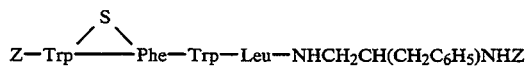

and

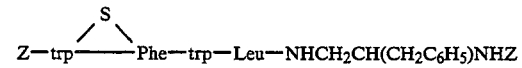

(mixture of isomers, 1.20 g.) with liquid hydrogen fluoride (25 ml.) and anisole (3.0 ml.) at 0° C. for 0.5 hr. and isolation of the product by stripping, ethyl acetate extraction, trituration with ether, lyophilization from acetic acid (900 mg. 100% yield) and relyophilization of part (200 mg.) from acetic acid gave

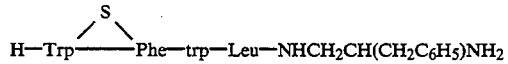

and

(mixture of isomers) diacetate salt dihydrate as an amorphous white solid.

EXAMPLE 14

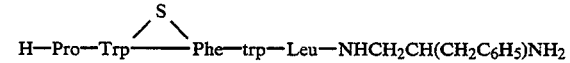

+

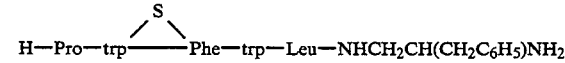

(mixture of isomers)

(mixture of isomers)
Condensation of Z-Pro-OSu (3.6 g.) and

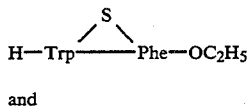

and

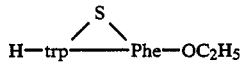

(example 7, mixtures of isomers, 4.0 g.) in tetrahydrofuran (60 ml.) at room temperature for 3 hr., isolation of the crude product by ethyl acetate extraction; and purification by HPLC on silica gel using ethyl acetate as eluant gave

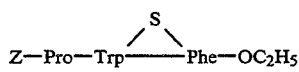

and

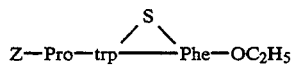

(mixture of isomers) as a white foam (5.2 g., 82% yield).

Hydrolysis of

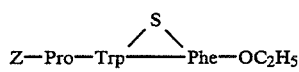

and

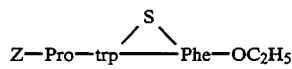

(mixture of isomers, 5.15 g.) with aqueous sodium hydroxide (2.5 N, 6.6ml.) in tetrahydrofuran (50 ml.) overnight, isolation of the crude product by ethyl acetate extraction, and purification by reverse phase HPLC on octadecylsilated silica gel using methanol-water (3:2) as eluant gave

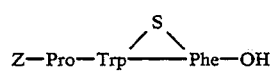

and

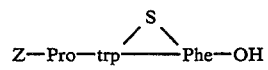

(mixture of isomers, 3.0 g., 61% yield).

Condensation of

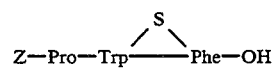

and

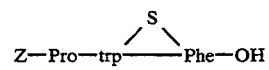

(mixture of isomers, 764 mg.) and H-trp-Leu-NHEH$_2$CH(CH$_2$C$_6$H$_5$)NHZ (example 13, 750 mg.) using diclohexylcarbodiimide (264 mg.) and N-hydroxysuccinimide (147 mg.) in tetrahydrofuran (25 ml.) at 0° C. for 0.5 hr. and then at room temperature overnight, isolation of the crude product by ethyl acetate extraction, and purification by HPLC on silica gel using hexane-ethyl acetate (25:75) as eluant gave

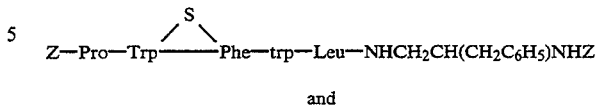

and

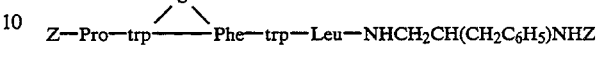

(mixture of isomers) as a foam (1.16 g., 78% yield).

De-(phenylmethoxy)carbonylation of

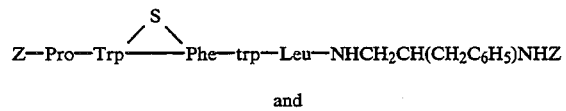

and

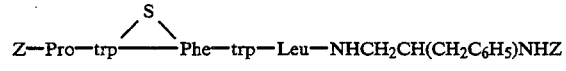

(mixture of isomers, 1.10 g.) with liquid hydrogen fluoride (25 ml.) and anisole (3.0 ml.) at 0° for 0.5 hr., isolation of the crude-product by stripping, and purification by column chromatography on silica gel using ethyl acetate-pyridine-acetic acid-water (200:54:16:30) as eluant followed by lyophilization from water gave

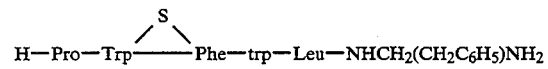

and

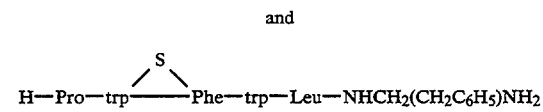

(mixture of isomers) phosphate (1: 2) salt heptahydrate as an amorphous white solid (578 mg., 51% yield).

EXAMPLE 15

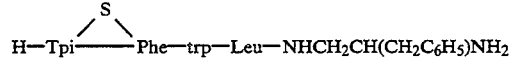
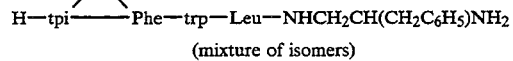

(mixture of isomers)

Condensation of

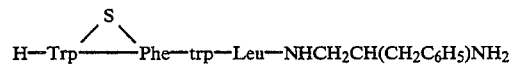

and

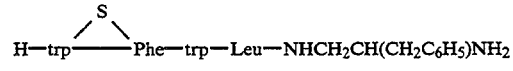

(example 13, mixture of isomers, 650 mg.) with formaldehyde (37%, 67 mg.) in acetic acid (25 mg.) at room temperature for 2 hr. and purification of the crude product by column chromatography (twice) on silica gel using ethyl acetate-pyridine-acetic acid water (400:54:16:30 first, 500:54:16:30 second) followed by lyophilization from acetic acid, conversion into the phosphate salt by ion exchange chromatography and lyophilization from acetic acid gave

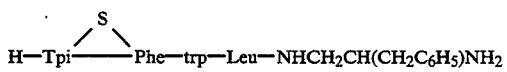

and

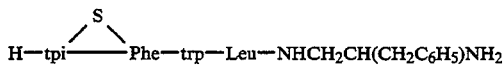

(mixture of isomers) phosphate (1:2) salt monoacetate monohydrate as an amorphous off-white solid (257 mg., 29!% yield).

EXAMPLE 16

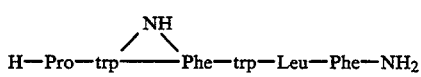

Cyclization of Z-trp-NH—CH(COC$_6$H$_5$)—COOCH$_3$ (part B of example 3, 10.0 g.) with ammonium acetate (50 g.) in acetic acid (100 ml.) with heating for 1.5 hr., isolation of the crude product by stripping the acetic acid and ethyl acetate extraction, and purification by HPLC on silica gel using hexane-ethyl acetate (45:55) as eluant gave

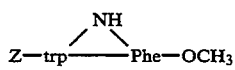

in 62% yield.
Hydrolysis of

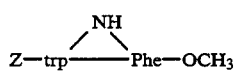

(6.0 g.) with aqueous sodium hydroxide (1.0 g. in 10 ml of water) in dioxane (50 ml.) for 4 hr. at steam bath temperature, isolation of the crude product by ethyl acetate extraction, and crystallization from ether gave

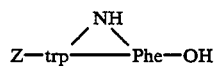

in two crops (2.7 g. , m.r. 142°-160° C.; 0.45 g. , m.r. 145°-160° C.; 54% yield).
Condensation of

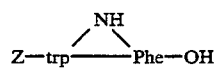

(750 mg.) and H-trp-Leu-Phe-NH$_2$ (example 2, 723 mg.) using dicyclohexylcarbodiimide (330 mg.) and N-hydroxysuccinimide (184 mg.) in tetrahydrofuran (20 ml.) at 0° C. and then at room temperature overnight, isolation by stripping the volatiles, and purification by column chromatography on silia gel using ethyl acetate as eluant gave

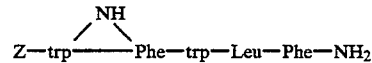

(730 mg., 51% yield).
De-(phenylmethoxy)carbonylation of

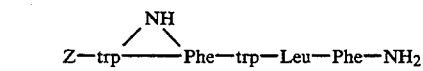

(675 mg.) by hydrogenation in a Parr shaker with palladium-on-carbon (10%, 100 mg.) in acetic acid (20 ml.) at room temperature for 7 hr., isolation of the product by filtration and lyophilization, purification by column chromatography on silica gel using ethyl acetate-pyridine-acetic acid-water (250:54:16:30) as eluant, and distribution between ethyl acetate and saturated aqueous sodium bicarbonate solution gave

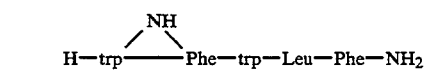

(390 mg., 68% yield).
Condensation of Boc-Pro-OSu (156 mg.) and

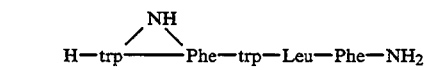

(370 mg.) in tetrahydrofuran (10 ml.) at room temperature for 2 days, isolation of the product by ethyl acetate extraction, and purification by HPLC on silica gel using ethyl acetate-isopropyl alcohol (95:5) as eluant gave

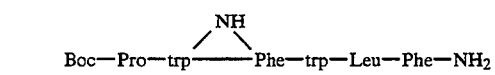

as an off-white foam (320 mg., 69% yield).
De-(1,1-dimethylethoxy)carbonylation of

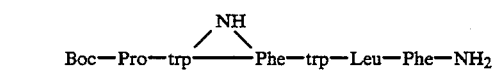

(300 mg.) using trifluoroacetic acid-water (70:30, 50 ml.) for 1.5 hr. at room temperature and isolation of the product by stripping, ethyl acetate extraction, dissolution in aqueous methanol containing hydrochloric acid (0.1N, 0.7 ml.), conversion into the phosphate salt by ion exchange chromatography and lyophilization from water gave

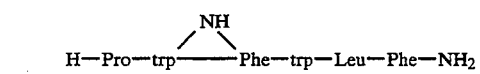

phosphate (2:1) salt as an amorphous white solid (203 mg., 66% yield).

EXAMPLE 17

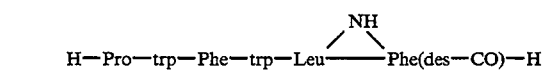

Condensation of Z-Leu-OH (26.5 g.) and H$_2$NCH$_2$COC$_6$H$_5$ hydrochloride salt (17.16 g.) by the mixed anhydride method using isobutyl chloroformate (13.66 g.) and triethylamine (two 10.12 g. portions) tetrahydrofuran (250 ml.) at −80° C. during the addition times and then at room temperature overnight, isolation of the crude product by filtration and stripping, and purification by crystallization from ether (first crop, 15.59 g., m.r. 95°-97 ° C.) and ether-hexane (second crop, 8.25 g., m.r. 95°-97° C.) and HPLC of the mother liquor on silica gel using hexane-ethyl acetate (70:30) as eluant followed by crystallization from ethyl acetate-hexane (third crop, 4.0 g., m.r. 96°-98° C.) gave Z-Leu-NH—CH$_2$—COC$_6$H$_5$ (73% yield).

Cyclization of Z-Leu-NH—CH$_2$—COC$_6$H$_5$ (10.0 g.) with ammonium acetate (50 g.) in acetic acid (100 ml.) under reflux for 8 hr., isolation of the crude product by stripping and ethyl acetate extraction; and purification by filtration through silica gel using hexane-ethyl acetate (7:3) as eluant followed by crystallization from ether-hexane gave

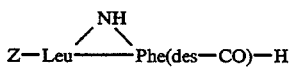

in two crops (5.31 g., m.r. 122°-124° C.; 300 mg.; 59% yield).

De-(phenylmethoxy) carbonylation of

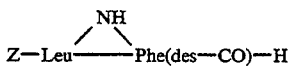

(4.25 g.) by hydrogenation in a Parr shaker with palladium-on-carbon (10%, 425 mg.) in acetic acid (50 ml.) at room temperature for 20 min. and isolation of the product by filtration, stripping, addition of hydrogen chloride (25 millimole in ethyl acetate) and precipitation from ethanol-ether gave

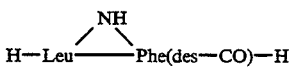

dihydrochloride salt hemihydrate as a white solid (3.22 g., 88% yield, m.r. 138°-150° C.).

Condensation of Boc-Pro-trp-Phe-trp-NHNH$_2$ (example 1, 1.40 g.) and

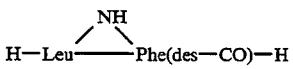

(freed from 582 mg. of the dihydrochloride salt hemihydrate with sodium bicarbonate) by the acyl azide method using butyl nitrite (0.218 ml.), hydrogen chloride in dimethylformamide (2.55 N, 0. 733 ml.) and diisopropylethylamine (482 mg.) in dimethylformamide (8 ml.) at 0° C. during mixing of the reactants and in the refrigerator overnight, isolation of the crude product by ethyl acetate extraction, and purification by filtration through silica gel using ethyl acetate as eluant gave

(1.17 g., 66% yield).

De-(1,1-dimethylethoxy)carbonylation of

(1.40 g.) using tri-fluoroacetic acid-water (70:30, 50 ml.) for 1.5 hr. at room temperature and isolation of the product by stripping, ethyl acetate extraction, stripping, addition of aqueous methanesulfonic acid (0.1145N, 25.85 ml.), methanol (10 ml.) and water (100 ml.), filtration and lyophilization gave

trimethanesulfonate salt monohydrate as an amorphous white solid (1.24 g. 73% yield).

EXAMPLE 18

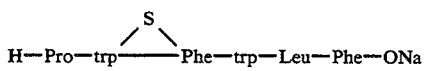

Condensation of Boc-trp-OH (30.5 g.) and methyl 2-amino-3-oxo-3-phenylpropionate hydrochloride salt (part B of example 3, 23.0 g.) by the mixed anhydride method using isobutyl chloroformate (13.69 g.) and N-methylmorpholine (two 11.02 ml. portions) in tetrahydrofuran at −30° C. during the addition times and for 15 min. thereafter and then at room temperature, isolation of the crude product by filtration and stripping, and purification by HPLC on silica gel using dichloromethane as injection solvent and hexane-ethyl acetate (1:1) as eluant gave Boc-trp-NH—CH(COC$_6$H$_5$)—COOCH$_3$ as a glass (29.5 g., 61% yield).

Cyclization of Boc-trp-NH—CH(COC$_6$H$_5$)—COOCH$_3$ (29.0 g.) with phosphorous pentasulfide (53.7 g.) in tetrahydrofuran at room temperature (exothermic reaction), isolation of the product by addition of sodium bicarbonate, stripping and ethyl acetate extraction; and purification by HPLC on silica gel using hexane-ethyl acetate (6:4) as eluant followed by crystallization from ether-hexane gave

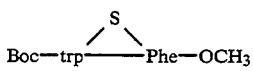

(6.27 g., 22% yield, 145°-147° C.).

Hydrolysis of

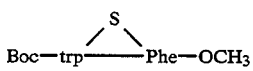

(8.4 g.) using aqueous sodium hydroxide (1N, 17.6 ml.) in dioxane (175 ml.) at room temperature overnight, isolation of the crude product by ethyl acetate extraction; and purification by crystallization from ether-hexane gave

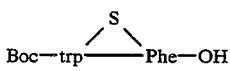

in two crops (7.26 g., m.r. 176°-177° C.; 289 mg., m.r. 172°-176° C.; 93% yield).

Condensation of Boc-trp-Leu-OH (part B of example of above-cited U.S. Pat. No. 4,472,305, 14.0 g.) and H-Phe-OBzl (freed from 14.33 g. of the p-toluenesulfonate salt with sodium bicarbonate) using dicyclohexylcarbodiimide (6.91 g.) and N-hydroxysuccinimide (3.86 g.) in tetrahydrofuran (250 ml.) at 0° C. for 1 hr. and then at room temperature overnight, isolation by ethyl acetate extraction, and purification by crystallization from methanol-ether-hexane gave Boc-trp-Leu-Phe-OBzl (16.9 g., 77% yield, m.r. 140°–142° C.).

De-(1,1-dimethylethoxy)carbonylation of Boc-trp-Leu-Phe-OBzl (16.5 g.) using trifluoroacetic acid-water (70:30, 150 ml.) for 1.25 hr. at room temperature and isolation of the product by stripping, ethyl acetate extraction and stripping from ether gave H-trp-Leu-Phe-OBzl as a glass.

Condensation of

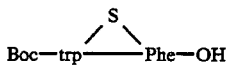

(1.50 g.) and H-trp-Leu-Phe-OBzl (1.30 g.) using dicyclohexylcarbodiimide (667 mg.) and N-hydroxysuccinimide (373 mg.) in tetrahydrofuran (50 ml.) at 0° C. during the addition times and then at room temperature for 1 hr., isolation of the crude product by ethyl acetate extraction, and purification by HPLC on silica gel using hexane-ethyl acetate (65:35) and then ethyl acetate alone as eluant gave

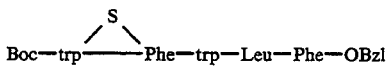

(2.3 g., 71% yield).

De-(1,1-dimethylethoxy)carbonylation of

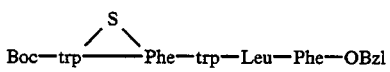

(2.20 g.) using trifluoroacetic acid-water (70:30, 50 ml.) for 1.25 hr. at room temperature, isolation of the product by ethyl acetate extraction, and purification by column chromatography on silica gel using ethyl acetate-pyridine-acetic acid-water (500:54:16:30) as eluant followed by crystallization from methanol-ether-hexane (first crop, 830 mg., m.r. 105°–108° C.) and acetic acid (0.5 ml.)-ethyl acetate (10 ml.)-ether (second crop 422 mg., m.r. 102°–105° C.) gave

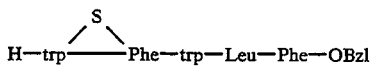

monoacetate salt (59% yield).

Condensation of Boc-Pro-OSu ( 234 mg.) and

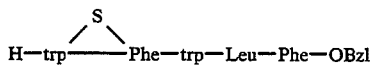

monoacetate salt (700 mg.) using diisopropylethylamine (94 mg.) in tetrahydrofuran (20 ml.) at room temperature for 5 days (the pH was adjusted to 8 after 1 hr.), isolation of the crude product by ethyl acetate extraction, and purification by HPLC on silica gel using hexane-ethyl acetate (35:65) as eluant gave

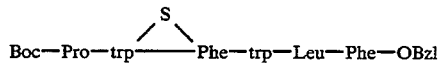

as a foam (660 mg., 83% yield).

Simultaneous de-(1,1-dimethylethoxy)carbonylation and debenzylation of

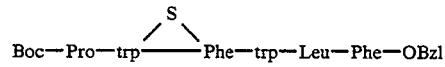

(500 mg.) with liquid hydrogen fluoride (25 ml.) and anisole (3.0 ml.) at ice-water temperature for 45 min. and isolation of the product by stripping, distribution between ethyl acetate and saturated aqueous sodium bicarbonate (the product appeared in the ethyl acetate layer but would not redissolve in ethyl acetate) and reprecipitation from methanol-ether gave

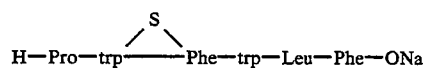

as an off-white solid (325 mg., 77% yield).

EXAMPLE 19

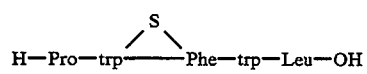

Condensation of Boc-trp-OSu ( 6.5 g.) and H-Leu-OBzl p-toluenesulfonate salt (6.37 g.) with diisopropylethylamine (2.09 g.) in tetrahydrofuran (100 ml.) at room temperature and isolation of the product by stripping and ethyl acetate extraction gave Boc-trp-Leu-OBzl as a foam (8.16 g., 997% yield).

De-( 1,1-dimethylethoxy) carbonylation of Boc-trp-Leu-OBzl (8.16 g.) using trifluoroacetic acid-water (70:30, 100 ml.) for 1.5 hr. at room temperature, isolation of the crude product (6.43 g.) by stripping and ethyl acetate extraction, and purification by reverse phase HPLC on octadecylsilated silica gel using methanol-water (3:1) as eluant gave H-trp-Leu-OBzl as a foamy gum (3.0 g., 46% yield).

Condensation of

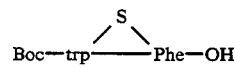

(example 18, 1.50 g.) and H-trp-Leu-OBzl (1.32 g.) using dicyclohexylcarbodiimide (667 mg.) and N-hydroxysuccinimide (373 mg.) in tetrahydrofuran (30 ml.) at 0° C. for 1 hr. and then at room temperature overnight and isolation of the crude product by filtration, stripping and filtration through silica gel with ethyl acetate-hexane (1:1) gave

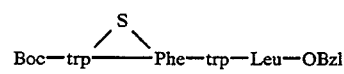

as a foam (2.82 g., theory, 2.76 g.) which crystallized in part (1.0 g., m.r. 105°–112° C.) from ether-hexane.

De-(1,1-dimethylethoxy)carbonylation of

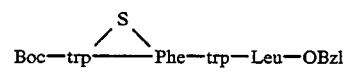

(2.5 g.) using trifluoroacetic acid-water (70:30, 50 ml.) for 1.5 hr. at room temperature and isolation of the product by stripping and ethyl acetate extraction gave

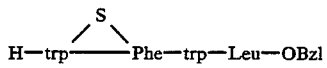

as a foam (2.17 g., 98% yield).

Condensation of Boc-Pro-OSu (468 mg.) and

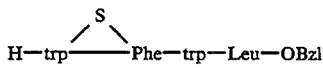

(1.0 g.) in tetrahydrofuran (20 ml.) at room temperature for 4 days, isolation of the crude product by ethyl acetate extraction; and purification by HPLC on silica gel using ethyl acetate-hexane (65:35) as eluant gave

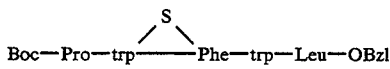

as a foam (1.05 g., 83% yield).

Simultaneous de-(1,1-dimethylethoxy)carbonylation and debenzylation of

Boc—Pro—trp⟨S⟩Phe—trp—Leu—OBzl (850 mg.) with liquid hydrogen fluoride (30 ml.) and anisole (5.0 ml.) at 0° C. for 45 min., isolation of the crude product by stripping, ethyl acetate extraction and reprecipitation from methanol-ether, and purification by column chromatography on silica gel using ethyl acetate-pyridine-acetic acid-water (200:54:16:30) as eluant gave H—Pro—trp⟨S⟩Phe—trp—Leu—OH acetate (2:5) salt solvate as the major less polar component.

EXAMPLE 20

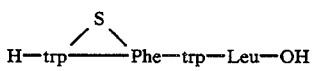

Debenzylation of

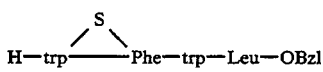

(example 19, 1.0 g.) with liquid hydrogen fluoride (35 ml.) and anisole (6 ml.) at 0° C. for 45 min. and isolation and purification of the product by stripping, dissolving the residue in a minimal amount of methanol and precipitating with ether in two crops (590 mg., 210 mg.), column chromatography on silica gel using ethyl acetate-pyridine-acetic acid-water (200:54:16:30) and lyophilization from acetic acid gave

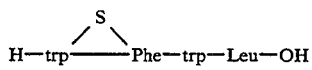

(2:5) salt solvate as an amorphous white solid (115 mg., 11% yield).

EXAMPLE 21

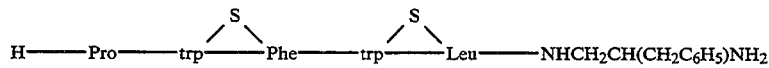

De-(phenylmethoxy)carbonylation of

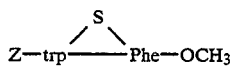

(part B of example 3, 20.0 g.) with liquid hydrogen fluoride (40 ml.) and anisole (25 ml.) at 0° C. for 30 min. and isolation of the product by stripping, washing with hexane-ether, ethyl acetate extraction, precipitation of a first crop as the hydrochloride salt (5.69 g.) with hydrogen chloride in ethyl acetate (4.4 N, 10 ml.), and basification of the filtrate with saturated aqueous sodium bicarbonate to give a second crop as the free base (2.3 g.) gave H—trp⟨S⟩Phe—OCH3 in 51% yield.

Condensation of Boc-Pro-OSu (6.05 g.) and

H—trp⟨S⟩Phe—OCH3

(5.50 g. as the hydrochloride salt, 2.30 g. as the free base) with N-methylmorpholine <1.53 g.) in tetrahydrofuran (100 ml.) at room temperature overnight, isolation of the crude product by ethyl acetate extraction, and purification by filtration through silica gel with ethyl acetate-hexane (1: 1) and HPLC on silica gel using ethyl acetate-hexane (3:1) as eluant gave

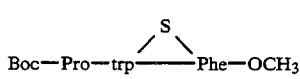

as a foam (7.0g., perhaps incorrectly weighed, 63% yield).

Hydrolysis of

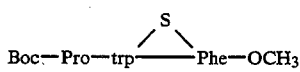

(6.9 g., perhaps incorrectly weighed) with aqueous sodium hydroxide (2.5N, 4.8 ml. initially and 3.0 ml. after 3 days) in methanol (75 ml.) at room temperature for 4 days, and isolation of the product by extraction with ether, acidification with citric acid, extraction with ethyl acetate and trituration with tetrachloromethane gave

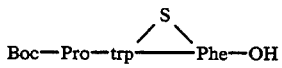

as a tan solid (7.18 g., theory 6.73 g. based on 6.9 g. of starting material).

By a method similar to that of part B of example $NH_2$—$CH(COCH(CH_3)_2)$—$COOCH_3$ hydrochloride salt was prepared in 95% yield from equimolar amounts of $(C_6H_5)_2C=N-CH_2-COOCH_3$ and $(CH_3)_3COK$ and a slightly greater (3%) than equimolar amount of $(CH_3)_2CH-COCl$.

Condensation of Boc-trp-OH (50.0 g.) and $NH_2$ $CH(COCH(CH_3)_2)$—$COOCH_3$ hydrochloride salt (32.14 g.) by the mixed anhydride method using isobutyl chloroformate (21.37 ml.) and N-methylmorpholine (two 18.9 g. portions) in tetrahydrofuran (500 ml.) for 0.5 hr. at $-20°$ C. and then at room temperature, isolation of the crude product by filtration and ether extraction, and purification by HPLC on silica gel using hexane-ethyl acetate as eluant followed by crystallization from ether-hexane gave Boc-trp-NH—CH-$(COCH(CH_3)_2)$—$COOCH_3$ as a white solid in two crops (43.0 g., m.r. 70°-72° C.; 11.6 g., m.r.63°-70° C.; 75% yield).

Cyclization of Boc-trp-NH—CH(COCH(CH$_3$)$_2$)—COOCH$_3$ (10.0 g.) with Lawesson's reagent (4.6 g. initially and 1 g. more after 2 hr. of reflux) in tetrahydrofuran (500 ml.) for 7 hr. under reflux, isolation of the crude product by stripping, and filtration through silica gel with hexane-ethyl acetate (3:1) followed by purification by HPLC on silica gel using hexane-ethyl acetate (65:35) as eluant gave

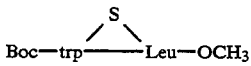

as a solid (6.7 g., 67% yield).

Hydrolysis of

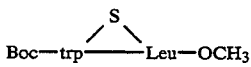

(12.0 g.) using aqueous sodium hydroxide (2.5N, 11.0 ml.) in methanol (50. ml) at room temperature for 2 days, isolation of the crude product by ether extraction of the basic reaction mixture followed by acidification and then ethyl acetate extraction, and purification by crystallization from ethyl acetate-hexane gave

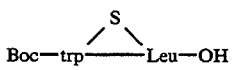

as a tan solid (5.50 g., m.r. 101°-104° C.; 5.36 g. more product obtained by stripping mother liquor; 93% yield).

Condensation of

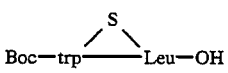

(3.02 g.) and $H_2NCH_2CH(CH_2C_6H_5)NHZ$ (example 13, 2.0 g.) by the mixed anhydride method using isobutyl chloroformate (960 mg.) and N-methylmorpholine (711 mg.) in tetrahydrofuran (50 ml.) for 45 min. at $-25°$ C. and then for 2 hr. at room temperature, isolation of the crude product (5.1 g.) by ethyl acetate extraction, and purification by crystallization from methanol-water gave

as a white solid (4.16 g., 85% yield, m.r. 92°-95° C.).

De-(1,1-dimethylethoxy)carbonylation of

(3.5 g.) using trifluoroacetic acid-water (70:30, 100 ml.) for 3 hr. at room temperature and isolation of the product by stripping, ethyl acetate extraction, treatment with hydrogen chloride in ethyl acetate (4.4N, 1.20 ml.) and precipitation with ether gave

hydrochloride salt as a tan solid (2.73 g., m.r. 128°-133° C., 86% yield).

Condensation of

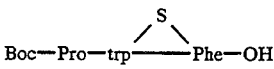

(1.00 g.) and

hydrochloride salt (948 mg.) using dicyclohexylcarbodiimide (309 mg.), N-hydroxysuccinimide (173 mg.) and diisopropylethylamine (194 mg.) in tetrahydrofuran (20 ml.) for 15 min. at 0° C. and then overnight at room temperature, isolation of the crude product by filtration and ethyl acetate extraction, and purification by HPLC on silica gel using ethyl acetate-hexane (3:2) as eluant gave

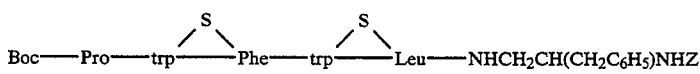

as a white foam (1.53 g., 89% yield).

Simultaneous de-(1,1-dimethylethoxy)carbonylation and de-(phenylmethoxy)carbonylation of

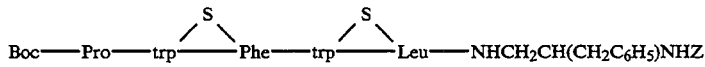

(1.48 g.) with liquid hydrogen fluoride (50 ml.) and anisole (7 ml.) at 0° C. for 0.5 hr. and isolation of the product by stripping, trituration with ether, conversion of a methanol-water (60:40) solution into the phosphate salt by ion exchange chromatography and lyophilization gave

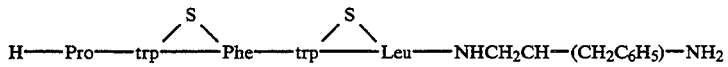

phosphate (2:3) salt hydrate (2:9) as an amorphous white solid (976 mg., 66% yield).

EXAMPLE 22

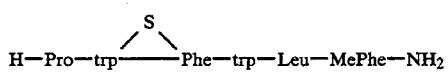

Condensation of Z-MePhe-OH (15.7 g.) and concentrated aqueous ammonia (5 ml., added last) by the mixed anhydride method using isobutyl chloroformate (7.0 ml.) and triethylamine (7.0 ml.) at −10° C. for 10 min., isolation of the crude product by ethyl acetate extraction, and purification by recrystallization from ethanol gave Z-MePhe-NH2 in two crops (9.63 g., m.r. 131°–133° C.; 2.05 g. , m.r. 132°–133° C.; 75% yield).

De-(phenylmethoxy)carbonylation of Z-MePhe-NH2 (11.5 g.) with hydrogen bromide in acetic acid (32%, 24 ml.) at 90° C. for 15 min., isolation of the crude product (8.95 g., m.r. 178°–205° C., 95% yield) by stripping and washing with ether, and purification by recrystallization from isopropyl alcohol-ether gave H-MePhe-NH2 hydrobromide salt (m.r. 206°–208° C.). Since racemization was discovered later in the synthesis, it is believed that it occurred at this or an earlier step and therefore that the product of this step was in fact H-MePhe-NH2 and H-Mephe-NH2 (mixture of isomers) hydrobromide salt.

Condensation of Boc-Leu-OH (liberated from 5.0 g. of the monohydrate by heating at 45° C. under vacuum) and H-MePhe-NH2 and H-MepheNH2 (mixture of isomers) hydrobromide salt (4.92 g.) and N-methylmorpholine (two 2.31 g. portions) in tetrahydrofuran (50 ml.) for 45 min. at 25° C. and then overnight at room temperature, isolation of the crude product (5.94 g.) by ethyl acetate extraction, and purification by HPLC on silica gel gave Boc-Leu-MePhe-NH2 and Boc-Leu-Mephe-NH2 (mixture of isomers) as a colorless foam (3.8 g., 48% yield).

De-(1,1-dimethylethoxy)carbonylation of Boc-Leu-MePhe-NH2 and Boc-Leu-Mephe-NH2 (mixture of isomers, 3.7 g.) with hydrogen chloride in ethyl acetate (4.4N, 25 ml.) for 2 hr. at room temperature and isolation of the product by precipitation with ether gave H-Leu-MePhe-NH2 and H-Leu-Mephe-NH2 (mixture of isomers) hydrochloride salt (2.63 g., 85% yield, m.r. 124°–127° C.).

Condensation of Boc-trp-OH (1.81 g.) and H-Leu-MePhe-NH2 and H-Leu-Mephe-NH2 (mixture of isomers) hydrochloride salt (1.95 g.) by the mixed anhydride method using isobutyl chloroformate (813 mg.) and N-methylmorpholine (two 685 mg. portions) in tetrahydrofuran (35 ml.) at −20° C. for 20 min. and then at room temperature briefly, isolation by ethyl acetate extraction, and purification by filtration through silica gel with ethyl acetate gave Boc-trp-Leu-MePhe-NH2 and Boc-trp-Leu-Mephe-NH2 (mixture of isomers) as white foam (2.70 g., 78% yield).

De-(1,1-dimethylethoxy)carbonylation of Boc-trp-Leu-MePhe-NH2 and Boc-trp-Leu-Mephe-NH2(mixture of isomers, 2.55 g.) using trifluoroacetic acid-water (70:30, 50 ml.) for 2 hr. at room temperature, isolation of the crude product by ethyl acetate extraction, and purification by crystallization from ethyl acetate-ether-hexane gave H-trp-Leu-MePhe-NH2 and H-trp-Leu-Mephe-NH2 (mixture of isomers) in three crops (661 mg., m.r. 130°–136° C.; 838 mg., m.r. −117° C.; 483 mg., m.r. 75°–85° C.; 94% yield).

Condensation in two runs of

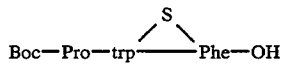

(example 21, 1.00 g. , 1.19 g.) and H-trp-Leu-MePhe -NH2 and H-trp-Leu-Mephe-NH2 (mixture of isomers, 850 mg. in both runs) using dicyclohexylcarbodiimide (367 mg. in both runs) and N-hydroxysuccinimide (205 mg. in both runs) in tetrahydrofuran (20 ml. in both runs) at 0° C. (1 hr., briefly) and then at room temperature (over the weekend, overnight), isolated by ethyl acetate extraction; and purified by HPLC on silica gel using ethyl acetate as eluant gave

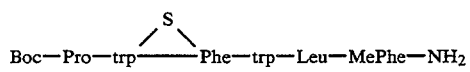

and

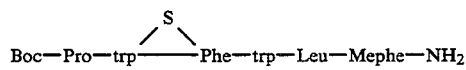

(mixture of isomers) as a white foam (1.01 g., 55% yield; 1.26 g., 69% yield).

De-(1,1-dimethylethoxy)carbonylation in two runs of

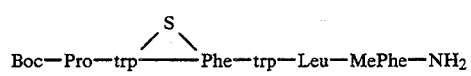

and

(mixture of isomers, 900 mg. , 1.10 g.) using trifluoroacetic acid-water (70:30, 25 ml., 50 ml.) at room temperature (2 hr., 1.5 hr.) and isolation of the crude product by ethyl acetate extraction gave

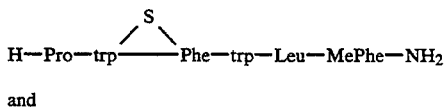

and

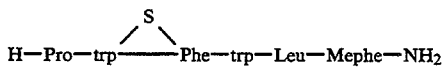

(mixture of isomers). Separation of the isomers involved several steps. In the first run the initial separation was by column chromatography an silica gel using ethyl acetate-pyridine-acetic acid-water (300:54:16:30) as eluant. In the second run the initial separation was by reverse phase HPLC an octadecylsilated silica gel using methanol-water (80:20) containing ammonium acetate (0.2%) as eluant. Corresponding fractions from both runs were then combined and separated further by column chromatography using tetrahydrofuran-acetic acid-water (94:3:3) as eluant. The final separation was by reverse phase HPLC on octadecylsilated silica gel using methanol-water (85:15) containing ammonium acetate (0.2%) as eluant, which after basification gave isomer A (220 mg.) and isomer B (180 mg.). Lyophilization of isomer A from acetic acid, conversion into the phosphate salt by ion exchange chromatography and lyophilization from water gave

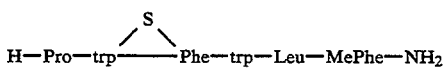

phosphate (1:1) salt trihydrate as an amorphous white solid (123 mg., 6% yield).

EXAMPLE 23

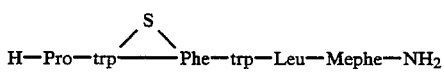

Lyophilization of isomer B (example 22, 180 mg.) from acetic acid, conversion into the phosphate salt by ion exchange chromatography and lyophilization from water-acetic acid (95:5) gave

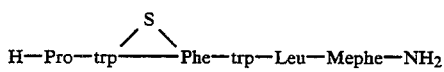

phosphate (1:2) salt dihydrate (103 mg. 5% yield)

EXAMPLE 24

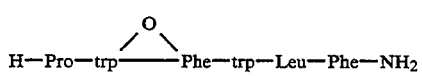

Cyclization of Z-trp-NH—CH(COC$_6$H$_5$)—COOCH$_3$ (15.0 g.) with diazabicycloundecene (13.1 ml.) and carbon tetrachloride (100 ml.) in pyridine (150 ml.) and acetonitrile (150 ml.) by dropwise addition of a solution of triphenylphosphine (23.0 g.) in pyridine (75 ml.) and acetonitrile (75 ml.) during 2 hr. at room temperature, isolation of the crude product by stripping, acidification with hydrochloric acid (0.5N, 1l.) and extraction with ethyl acetate (both layers were black), and purification by filtration through silica gel with ethyl acetate-hexane (1:1), HPLC on silica gel using hexane-ethyl acetate (45:55) as eluant, crystallization from methanol in two crops (4.58 g., m.r. 149°–151° C.; 0.22 g.), reverse phase HPLC of the mother liquor on octadecylsilated silica gel using methanol-water (70:30 as eluant) and crystallization from methanol (1.11 g., m.r. 151°–153° C.) gave

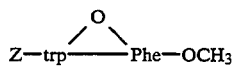

as a white solid (41% yield).

Hydrolysis of

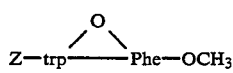

(4.41 g.) with aqueous sodium hydroxide (1N, 89 ml.) in dioxane (180 ml.) for 0.5 hr. at room temperature, isolation of the crude product by stripping, acidification with hydrochloric acid (1N, 9 ml.) and ethyl acetate extraction, and purification by crystallization from methanol gave

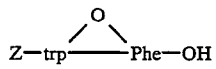

in two crops (2.28 g., m.r. 110°–115° C.; 1.88 g.; 97% yield).

Condensation of

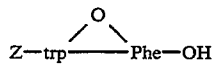

(2.00 g.) and H-trp-Leu-Phe-NH$_2$ (example 2, 1.93 g.) using dicyclohexylcarbodiimide (0.94 g.) and N-hydroxysuccinimide (0.48 g.) in tetrahydrofuran (30 ml.) initially at ice temperature and then at room temperature, isolation of the crude product by filtration, stripping and ethyl acetate extraction, and purification by HPLC on silica gel using ethyl acetate-hexane (90:10) as eluant gave

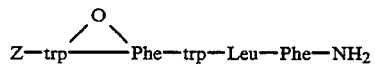

(2.07 g., 54% yield), part (390 mg.) of which was crystallized from dichloromethane (325 mg., m. r. 147°–152° C.).

De-(phenylmethoxy)carbonylation of

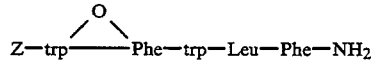

(1.52 g.) with liquid hydrogen fluoride (30°–40 ml.) and anisole (10 ml.) at 10° C. for 3 hr. while the hydrogen fluoride was being stripped, isolation of the crude product (1.18 g.) by ethyl acetate extraction, and purification by trituration with ethyl acetate (the crude product would not redissolve therein) gave

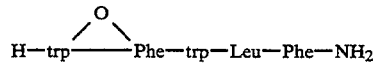

as a white solid in two crops (1.02 g., m.r. 145°–148° C.; 120 mg.; 88% yield).

Condensation of Boc-Pro-OSu (750 mg.) and

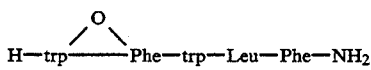

(950 mg.) with N-methylmorpholine (0.3 ml.) in tetrahydrofuran (7 ml.)-dimethylformamide (7 ml.) for 1 day at room temperature, isolation of the crude product by stripping and ethyl acetate extraction, and purification by HPLC on silica gel using ethyl acetate-isopropyl alcohol (98:2) gave

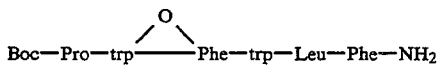

as a clear gum (1.06 g., 89% yield).

De-(1,1-dimethylethoxy)carbonylation of

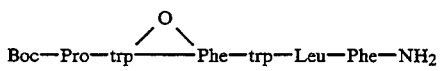

(980 mg.) using trifluoroacetic acid-water (80:20) for 1 hr. at room temperature, isolation by stripping and ethyl acetate extraction, and purification by reverse phase HPLC on octadecylsilated silica gel using methanol-water (78:22) containing ammonium acetate (0.2%) as eluant followed by lyophilization from acetic acid containing dilute hydrochloric acid gave

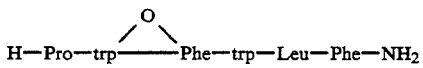

monohydrochloride salt monoacetate sesquihydrate as an amorphous white solid (750 mg., 75% yield).

EXAMPLE 25

Condensation of Boc-trp-Phe-OH (example 18, 1.21 g.) and

hydrochloride salt (example 21, 1.70 g.) using dicyclohexylcarbodiimide (554 mg.), N-hydroxysuccinimide (309 mg.) and diisopropylethylamine (348 mg.) at 0° C. and then at room temperature, isolation of the crude product by filtration and stripping, and purification by filtration through silica gel with ethyl acetate-hexane (1:1) and crystallization from ethyl acetate-hexane-ether gave

as a very slightly pink solid in two crops (1.27 g., m.r. 210°–212° C.; 82 mg., m.r. 205°–209° C.; 49% yield).

De-(1,1-dimethylethoxy)carbonylation of

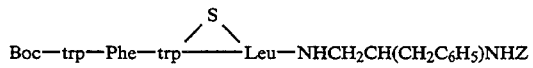

(1.30 g.) using trifluoroacetic acid-water (70:30, 50 ml.) for 3 hr. at room temperature and isolation of the product by stripping and ethyl acetate extraction gave

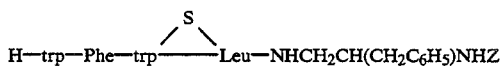

as a white foam (1.38 g.; theory, 1.17 g.).

Condensation of Boc-Pro-OSu (156 mg.) and

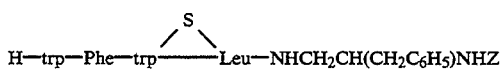

assumed to be 85% pure, 500 mg.) in tetrahydrofuran at room temperature overnight and then for an additional 2 hr. after addition of diisopropylethylamine (65 mg.), isolation of the crude product by stripping, and purification by filtration through silica gel using ethyl acetate-hexane (80:20) as eluant gave

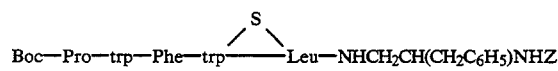

as a white foam containing about a half molar equivalent of ethyl acetate as shown by the NMR spectrum (460 mg., 86% yield).

Simultaneous de-(1,1-dimethoxy)carbonylation and de-(phenylmethoxy) carbonylation of

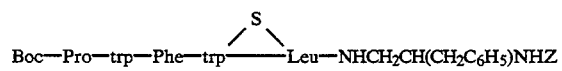

containing about a half molar equivalent of ethyl acetate (420 mg.) with liquid hydrogen fluoride (25 ml.) and anisole (5 ml.) at 0° C. for 0.5 hr. and isolation of the product by stripping, ethyl acetate extraction, lyophilization from acetic acid, conversion into the phosphate salt by ion exchange chromatography and lyophilization first from water and then from acetic acid gave

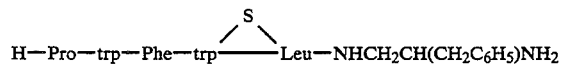

phosphate (1:2) salt diacetate dihydrate as an amorphous white solid (283 mg., 62% yield).

EXAMPLE 26

Condensation of

(example 21, 6.00 g.) and HN(CH₃)CH₂CH₂C₆H₅ (1.89 g.) using dicyclohexylcarbodiimide (2.88 g.) and N- hydroxysuccinimide (1.6 g.) in tetrahydrofuran (75 ml.) at 0° C. and then at room temperature, isolation of the crude product by filtration and stripping, and purification by filtration through silica gel with hexane-ethyl acetate (1:1) and HPLC on silica gel using hexane-ethyl acetate (1:1) as eluant gave

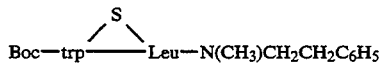

as a foam (4.93 g., 65% yield).
De-(1,1-dimethoxy)carbonylation of

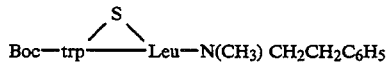

(4.8 g.) using trifluoroacetic acid-water (70:30, 150 ml.) for 2 hr. at room temperature and isolation of the product by stripping and ethyl acetate extraction gave

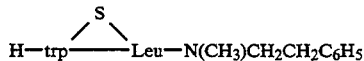

as a foam (3.90 g., 99% yield).
Reduction of

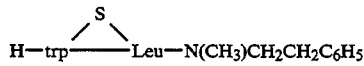

(3.80 g.) with diisobutylaluminum hydride (1.5 M in toluene, 28.4 ml.) in toluene (40 ml.), quenching with methanol (30 ml.), isolation of the crude product (4.04 g.) by ethyl acetate extraction, and purification by reverse phase HPLC on octadecylsilated silica gel using methanol-water (80:20) containing ammonium acetate (0.2%) as eluant gave

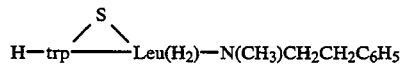

as a foam (1.42 g., 39% yield).
Condensation of Boc-trp-Phe-OH (example 18, 1.46 g.) and

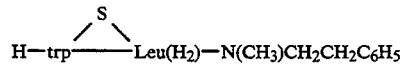

(1.40 g.) using dicyclohexylcarbodiimide (667 mg.) and N-hydroxysuccinimide (373 mg.) in tetrahydrofuran (20 ml.) at 0° C. and then at room temperature, isolation of the crude product by filtration and ethyl acetate extraction and crystallization from ether and ether-hexane gave

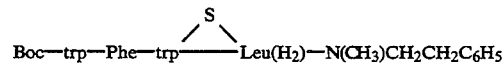

in three crops (803 mg., m.r. 123°–126° C.; 893 mg., m.r. 120°–125° C.; 380 mg., m.r. 118°–123° C.; 74% yield).
De-(1,1-dimethylethoxy)carbonylation of

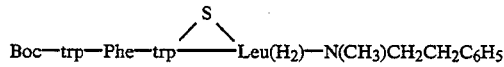

(2.0 g.) using trifluoroacetic acid-water (70:30, 100 ml.) for 1.5 hr. at room temperature and isolation of the product by stripping and ethyl acetate extraction gave

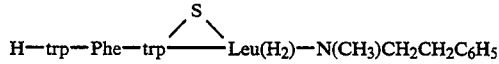

as a pale yellow foam (1.85 g.; theory, 1.77 g.).
Condensation of

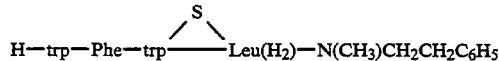

(500 mg.) and formaldehyde (37%, 53 μl.) in acetic acid (50 ml.) at room temperature for 1 hr., isolation of the crude product by stripping, and purification by reverse phase HPLC on octadecylsilated silica gel using methanol-water (82.5:17.5) containing 0.2% ammonium acetate, lyophilization from acetic acid, conversion into the phosphate salt by ion exchange chromatography and lyophilization first from water and then from acetic acid gave

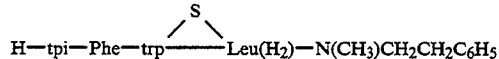

phosphate (1:2) salt sesquiacetate hemihydrate as an amorphous white solid (237 mg., 34% yield).

EXAMPLE 27

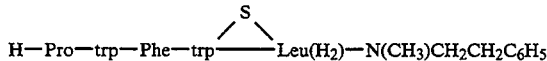

Condensation of Boc-Pro-OSu (219 mg.)

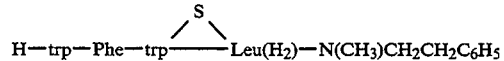

(example 26, 500 mg.) in tetrahydrofuran at room temperature overnight, isolation of the crude product by stripping, and purification by HPLC on silica gel using ethyl acetate-isopropyl alcohol (98:2, then 95:5, then 90:10) gave

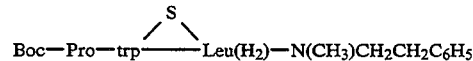

(510 mg., 81% yield).
De-(1,1-dimethylethoxy)carbonylation of

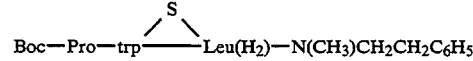

(450 mg.) using trifluoroacetic acid-water (70:30, 50 ml.) at room temperature for 1.5 hr. and isolation of the product by stripping, ethyl acetate extraction and lyophilization from water containing hydrochloric acid (0.95 N, 1.0 ml.) gave

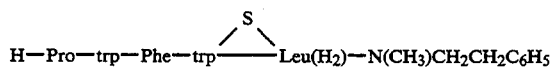

dihydrochloride salt hydrate (2:5) as an amorphous white solid (390 mg., 85% yield).

EXAMPLE 28

Condensation of

(example 25, assumed to be 85% pure, 450 mg.) and formaldehyde (37%, 41 μl) in acetic acid at room temperature for 2 hr., isolation of the crude product by stripping, and purification by flash chromatography on silica gel using ethyl acetate-pyridine-acetic acid-water (700:54:16:30) as eluant gave

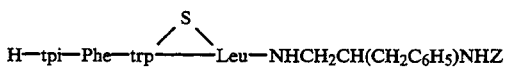

(183 mg., assumed to be the monoacetate salt, 52% yield).

De-(phenylmethoxy)carbonylation in two runs of

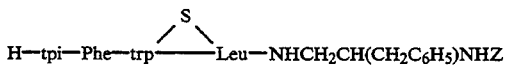

(assumed to be the monoacetate salt, 300 mg., 183 mg.) with liquid hydrogen fluoride (20 ml., 30 ml.) and anisole (5.0 ml., 5.0 ml.) at 0° C. for 0.5 hr., isolation of the crude product by stripping (and in the second run also by ethyl acetate extraction), and purification of the combined products of both runs (after partially purifying the crude product of the first run by reverse phase HPLC on octadecylsilated silica gel using 80:20 methanol-water containing 0.2% ammonium acetate as eluant) by column chromatography on silica gel using ethyl acetate-pyridine-acetic acid-water (250:54:16:30) followed by ethyl acetate extraction with sodium bicarbonate washing of the resulting foam (183 mg.) and lyophilization from water containing hydrochloric acid (1N, 0.4 ml.) gave

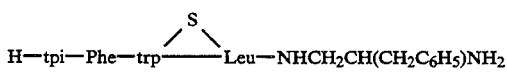

dihydrochloride salt as an amorphous off-white solid, part (124 mg.) as the sesquiacetate sesquihydrate and part (42 mg.) as the diacetate (32% yield).

BIOLOGICAL PROPERTIES OF THE COMPOUNDS

As stated above the azole-fused peptides of Formula I are useful as Substance P antagonists and analgesics or as synthetic intermediates therefor. These biological properties are demonstrated by a test for Substance P antagonist effect in the isolated guinea pig ileum and a test for acetylcholine-induced writhing in the mouse.

Guinea Pig Ileum Test

Strips of longitudinal muscle (derived from terminal ileum of adult male guinea pigs (Charles River, 400–600 g.) are mounted in 5-ml. organ baths containing oxygenated Krebs solution containing 1 μM each of atropine and pyrilamine maintained at 30°–33° C. and connected to isometric transducers. Following tissue equilibration and repeated washing (45–60 min.), SP or an appropriate reference agonist is added cumulatively to the bath and contractions of the tissue are recorded. The bath is washed thoroughly and 30–45 min. is allowed to elapse before construction of a second reference agonist curve to assure reproducibility of the responses. Test compounds are similarly evaluated for agonist activity up to a maximum concentration of 10–100 μM. Regression analysis of the linear portion of the log concentration-percent maximal response curves provides the EC50 (and 95% confidence limits), the standard measure of agonist potency. When appropriate, relative molar potency ratios are calculated (EC50 reference/ED50 test drug). Antagonist activity is examined by pretreating thoroughly washed tissues with test compound (using a standard 5–10 min. contact time), then constructing a cumulative dose-response curve to the reference agonist. The effects of several concentrations of test antagonist, pooled across separate experiments, provide dose-ratio (EC50 shift) data for a standard Schild plot analysis, with computation of the $pA_2$.

The following results were obtained for the title compounds (final products) of examples 1–28.

TABLE I

| Guinea Pig Ileum Test Results | |
|---|---|
| Final Product of Example | Substance P Antagonist $pA_2$ |
| 1 | 5.5[a] |
| 2 | 6.9 |
| 3 | 7.3 |
| 4 | 6.3 |
| 5 | 6.9 |
| 6 | 5.9 |
| 7 | <5[a] |
| 8 | 5.1[a] |
| 9 | 5.3[a] |
| 10 | 5.9 |
| 11 | 5.1 |
| 12 | 5.3 |
| 13 | 5.8[b] |
| 14 | 6.8 |
| 15 | 5.5 |
| 16 | 6.7 |
| 17 | 6.3 |
| 18 | 6.5[b] |
| 19 | <5 |
| 20 | <5 |
| 21 | <5 |
| 22 | 7.1 |
| 23 | 6.7 |
| 24 | 6.2[b] |
| 25 | 6.1 |
| 26 | ≦5 |
| 27 | ≦5 |
| 28 | 5.8 |

[a]Limited data due to solubility
[b]Slope significantly different from −1

Mouse Acetylcholine-induced Writhing Test

Male Swiss-Webster mice (18°–24 g.) are divided into groups of 8–15 mice. A test compound in a vehicle or the vehicle alone is administered intravenously in a volume of 0.01 ml./g. or intrathecally in a volume of μl by the method of Hylden and Wilcox (European Journal of Pharmacology, vol. 67, pp. 313–316, 1980) except that for the intrathecal route caudal cutaneous incision is not performed prior to injection. Five minutes after the injection a solution of acetylcholine (3.2 mg./kg., the ED90–100) in 0.9% aqueous sodium chloride is administered intraperitoneally to each mouse. A mouse not exhibiting one or more writhes during the next two-minute observation period is considered protected by the test compound. For test compounds which produce a graded dose-response ED5C values with 95% confidence limits are determined by probit analysis of the data.

The following results were obtained for the title compounds (final products) of examples 2 and 3.

| Final Product of Example | Intrathecal ED50 (μg/mouse) | Intravenous ED50 (mg./kg.) |
| --- | --- | --- |
| 2 | 1.7 | 9.9 |
| 3 | 0.78 | 11 |

The substance P antagonists and analgesics of Formula I can be prepared for oral or parental administration in liquid or solid dosage form as solutions, suspensions, emulsions, capsules or tablets or in any other suitable dosage form with conventional pharmaceutical vehicles and adjuncts by conventional pharmaceutical techniques.

We claim:

1. An azole-fused peptide having the structural formula

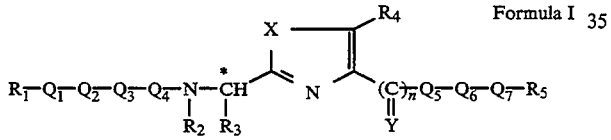

Formula I wherein
  $Q_1$ is L-prolyl or a direct linkage;
  $Q_2$ is L-prolyl, D-tryptophyl or a direct linkage;
  $Q_3$ is L-prolyl, D-tryptophyl, L-phenylalanyl, R-(2,3,4,9-tetrahydro-1H-pyrido[3,4-b]indol-2-yl-3-carbonyl) or a direct linkage;
  $Q_4$ is L-prolyl, D-tryptophyl, L-phenylalanyl or a direct linkage;
  $Q_5$ is L-prolyl, D-tryptophyl or a direct linkage;
  $Q_6$ is L-leucyl, L-methionyl or a direct linkage;
  $Q_7$ is L-phenylalanyl, N-methyl-L-phenylalanyl, L-methionyl or a direct linkage;
  $R_1$ is a hydrogen atom, (phenylmethoxy)carbonyl or (1,1-dimethylethoxy)carbonyl;
  $R_2$ taken alone is a hydrogen atom;
  $R_3$ taken alone is 1-methylethyl, 2-methylpropyl, 4-aminobutyl, phenylmethyl, 4-hydroxyphenylmethyl, pyridylmethyl or (1H-indol-3-yl)methyl; or
  $R_2$ taken together with N, CH and $R_3$ is 2,3,4-9-tetrahydro-1H-pyrido[3,4-b]indol-2,3-diyl);
  $R_4$ is ethyl, propyl, 1-methylethyl, methylthiomethyl, ethylthiomethyl, phenyl, 4-hydroxyphenyl, pyridyl or 1H-indol-3-yl;
  $R_5$ is a hydrogen atom when n is 0 and $Q_5$, $Q_6$ and $Q_7$ are each a direct linkage; hydroxy or an alkali metal salt thereof, methoxy, ethoxy, 1,1-dimethylethoxy, amino, methylamino, dimethylamino, 2-(dimethylamino)ethylamino, (2-amino-3-phenylpropyl)amino or N-methyl-2-phenylethylamino when Y is oxo and n is 1; or hydroxy or an alkali metal salt thereof, amino, methylamino, dimethylamino, 2-(dimethylamino)ethylamino, (2-amino-3-phenylpropyl)amino, 2-amino-2-(phenylmethyl)ethylamino or N-methyl-2-phenylethylamino when Y is two separately bonded hydrogen atoms, n is 1 and $Q_5$, $Q_6$ and $Q_7$ are each a direct linkage;
  X is oxa, thia or imido;
  Y is oxo or two separately bonded hydrogen atoms;
  n is 0 or 1;
  * is L or D; and
wherein at least two of $Q_1$, $Q_2$, $Q_3$ and $Q_4$, or $Q_5$, $Q_6$ and $Q_7$ are other than a direct linkage; or a pharmaceutically acceptable acid addition salt thereof.

2. An azole-fused peptide of Formula I according, to claim 1 wherein $Q_1$ is L-prolyl and $R_1$ and $R_2$ are each a hydrogen atom.

3. An azole-fused peptide of Formula I according to claim 2 wherein $R_3$ is (1H-indol-3-yl)methyl, Y is oxo and n is 1.

4. An azole-fused peptide of Formula I according to claim 3 wherein $Q_2$, $Q_3$, and $Q_4$ are each a direct linkage, $Q_5$ is D-tryptophyl, $Q_6$ is L-leucyl and $R_4$ is phenyl.

5. An azole-fused peptide of Formula I according to claim 4 wherein $Q_7$ is L-phenylalanyl and $R_5$ is amino or hydroxy or an alkali metal salt thereof.

6. An azole-fused peptide of Formula I according to claim 5 wherein $R_5$ is amino and X is thia.

7.

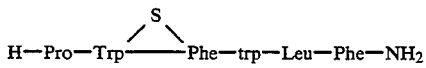

having the structural formula

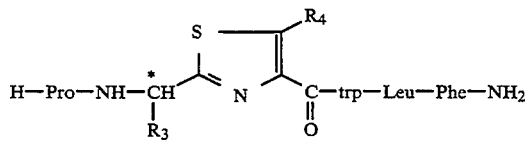

wherein $R_3$ is (1H-indol-3-yl)methyl, $R_4$ is phenyl and * is L or a pharmaceutically acceptable acid addition salt and/or solvate thereof according to claim 6.

8.

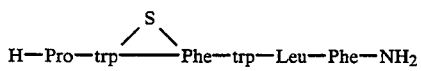

having the structural formula

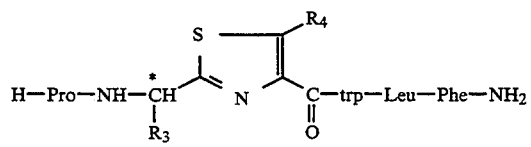

Wherein $R_3$ is (1H-indol-3-yl)methyl, $R_4$ is phenyl and * is D or a pharmaceutically acceptable acid addition salt and/or solvate thereof according to claim 6.

9. An azole-fused peptide of Formula I according to claim 5 wherein $R_5$ is hydroxy or an alkali metal salt thereof and X is thia.

10. The azole-fused peptide

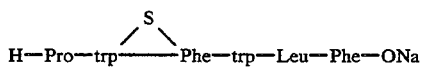

having the structural formula

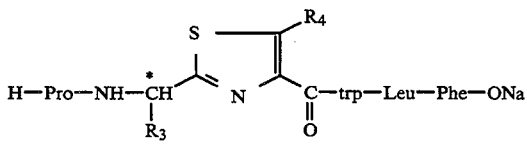

wherein $R_3$ is (1H-indol-3-yl)methyl, $R_4$ is phenyl and * is D or a pharmaceutically acceptable acid addition salt and/or solvate thereof according to claim 9.

11. An azole-fused peptide of Formula I according to claim 5 wherein $R_5$ is amino and X is imido.

12. The azole-fused peptide

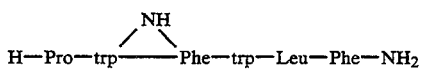

having the structural formula

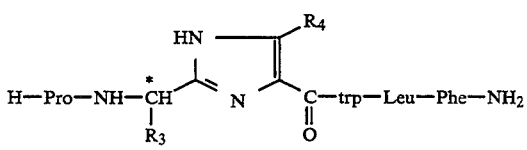

wherein $R_3$ is (1H-indol-3-yl)methyl, $R_4$ is phenyl and * is D or a pharmaceutically acceptable acid addition salt and/or solvate thereof according to claim 11.

13. An azole-fused peptide of Formula I according to claim 5 wherein $R_5$ is amino and X is oxa.

14. The azole-fused peptide

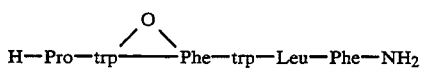

having the structural formula

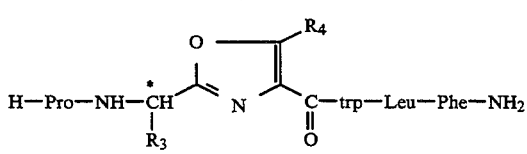

wherein $R_3$ is (1H-indol-3-yl)methyl, $R_4$ is phenyl and * is D or a pharmaceutically acceptable acid addition salt and/or solvate thereof according to claim 13.

15. An azole-fused peptide of Formula I according to claim 4 wherein $Q_7$ is N-methyl-L-phenylalanyl, $R_5$ is amino and X is thia.

16. The azole, fused peptide

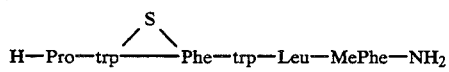

having the structural formula

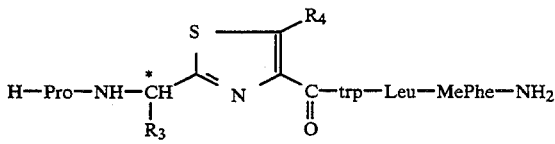

wherein $R_3$ is (1H-indol-3-yl)methyl, $R_4$ is phenyl and * is D or a pharmaceutically acceptable acid addition salt and/or solvate thereof according to claim 15.

17. The azole-fused peptide

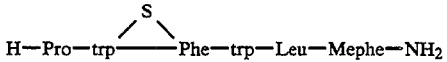

having the structural formula

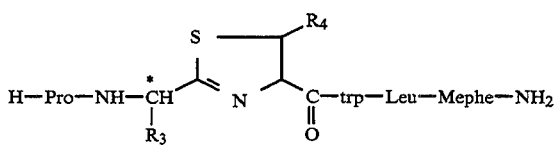

wherein $R_3$ is (1H-indol-3-yl)methyl, $R_4$ is phenyl and * is D or a pharmaceutically acceptable acid addition salt and/or solvate thereof according to claim 15.

18. An azole-fused peptide of Formula I according to claim 3 wherein $Q_2$ is D-tryptophyl, $Q_3$ is L-phenylalanyl, $Q_4$, $Q_6$ and $Q_7$ are each a direct linkage, $Q_5$ is L-phenylalanyl, $R_4$ is 1-methylethyl, $R_5$ is amino and X is thia.

19. The azole-fused peptide

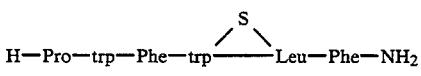

having the structural formula

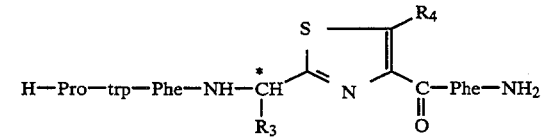

wherein $R_3$ is (1H-indol-3-yl)methyl, $R_4$ is 1-methylethyl and * is D or a pharmaceutically acceptable acid addition salt and/or solvate thereof according to claim 18.

20. The azole-fused peptide

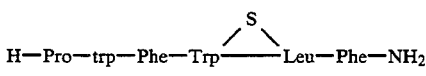

having the structural formula

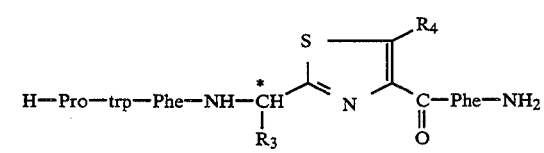

wherein R₃ is (1H-indol-3-yl)methyl, R₄ is 1-methylethyl and * is L or a pharmaceutically acceptable acid addition salt and/or solvate thereof according to claim 18.

21. An azole-fused peptide of Formula I according to claim 3 wherein R₅ is (2-amino-3-phenylpropyl)amino and X is thia.

22. An azole-fused peptide of Formula I according to claim 21 wherein Q₂, Q₃, Q₄ and Q₇ are each a direct linkage, Q₅ is D-tryptophyl, Q₆ is L-leucyl and R₄ is phenyl.

23. The azole-fused peptide

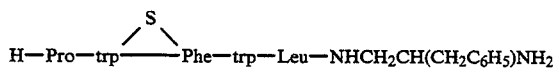

having the structural formula

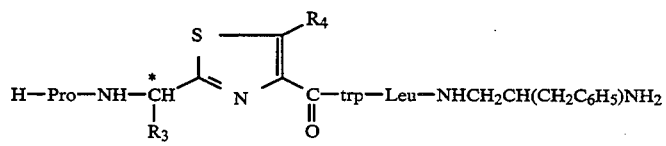

wherein R₃ is (1H-indol-3-yl)methyl, R₄ is phenyl and * is D or a pharmaceutically acceptable acid addition salt and/or solvate thereof according to claim 22.

24. An azole-fused peptide of Formula I according to claim 21 wherein Q₂ is D-tryptophyl, Q₃ is L-phenylalanyl, Q₄Q₅, Q₆, and Q₇ are each a direct linkage and R₄ is 1-methylethyl.

25. The azole-fused peptide

having the structural formula

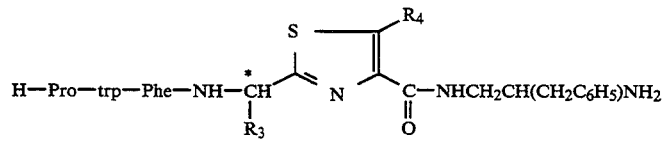

wherein R₃ is (1H-indol-3-yl)methyl, R₄ is 1-methylethyl and * is D or a pharmaceutically acceptable acid addition salt and/or solvate thereof according to claim 24.

26. An azole-fused peptide of Formula I according to claim 2 wherein Q₂ and Q₄ are each D-tryptophyl, Q₃ is L-phenylalanyl, Q₅, Q₆, and Q₇ are each a direct linkage, R₃ is 2-methylpropyl, R₄ is phenyl, R₅ is a hydrogen atom, X is imido and n is 0.

27. The azole-fused peptide

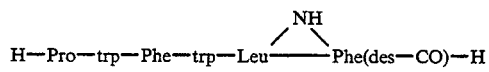

having the structural formula

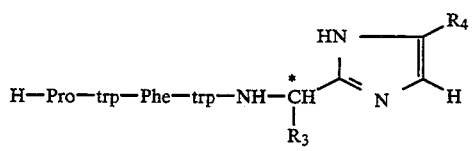

wherein R₃ is 2-methylpropyl, R₄ is phenyl and * is L or a pharmaceutically acceptable acid addition salt and/or solvate thereof according to claim 26.

28. The process of preparing an azole-fused peptide of Formula I wherein X is thia according to claim 1 which comprises the step of oxidizing with 2,3-dichloro-5,6-dicyanoquinone in an inert solvent selected from the group consisting of water, alcohols, acids, nitriles, amides and ethers or mixture thereof at a temperature in the range of 0°–1000° C. the corresponding peptide having the structural formula

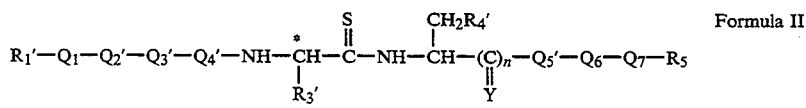

wherein
Q₂' is L-prolyl or a direct linkage;
Q₃' is L-prolyl, L-phenylalanyl or a direct linkage;
Q₄' is L-prolyl, L-phenylalanyl or a direct linkage;
Q₅' is L-phenylalanyl or a direct linkage;
R₁' is the same as defined for R₁ in Formula I except that R₁' cannot be a hydrogen atom when Q₁', Q₂', Q₃' and Q₄' are each a direct linkage;
R₃' is 1-methylethyl, 2-methylpropyl or phenylmethyl;
R₄' is 1H-indol-3-yl; and
Q₁, Q₆, Q₇, R₅, Y, n and * are the same as defined for Formula I.

29. The process of preparing a peptide having the structural formula

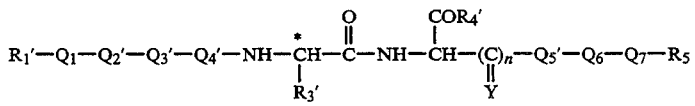

Formula III which comprises the step of oxidizing with 2,3-dichloro-5-6-dicyanoquinone in water or a mixture of water and an inert solvent selected from the group Consisting of alcohols, acids, nitriles, amides and ethers at a temperature in the range of 0°-100° C., the corresponding peptide having the structure

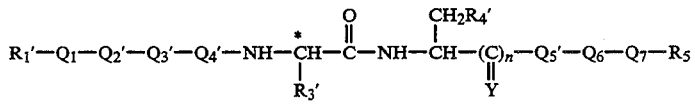

Formula IV wherein
$Q_1$ is L-prolyl or a direct linkage;
$Q_{2'}$ is L-prolyl or a direct linkage;
$Q_{3'}$ is L-prolyl, L-phenylalanyl or a direct linkage;
$Q_{4'}$ is L-prolyl, L-phenylalanyl or a direct linkage;
$Q_{5'}$ is L-phenylalanyl or a direct linkage;
$Q_6$ is L-leucyl, L-methionyl or a direct linkage;
$Q_7$ is L-phenylalanyl, N-methyl-L-phenylalanyl, L-methionyl or a direct linkage;
$R_1'$ is a hydrogen atom, (phenylmethoxy)carbonyl or (1,1-dimethylethoxy)carbonyl except that $R_1'$ cannot be a hydrogen atom when $Q_1$, $Q_2'$, $Q_3'$ and $Q_4'$ are each a direct linkage;
$R_3'$ is 1-methylethyl, 2-methylpropyl or phenylmethyl;
$R_4'$ is 1H-indol-3-yl; $R_5$ is a hydrogen atom when n is 0 and $Q_5'$, $Q_6$ and $Q_7$ are each a direct linkage; hydroxy or an alkali metal salt thereof, methoxy, ethoxy, 1,1-dimethylethoxy, amino, methylamino, dimethylamino, 2-(dimethylamino)ethylamino, (2-amino-3-phenylpropyl)amino or N-methyl-2-phenylethyl-amino when Y is oxo and n is 1; or hydroxy or an alkali metal salt thereof, amino, methylamino, dimethylamino, 2-(dimethylamino)ethylamino, (2-amino-3-phenylpropyl)-amino, 2-amino-1-phenylmethyl)ethylamino, or N-methyl-2-phenylethylamino when Y is two separately bonded hydrogen atoms, n is 1 and $Q_5'$, $Q_6$ and $Q_7$ are each a direct linkage;
Y is oxo or two separately bonded hydrogen atoms;
n is 0 or 1; and
* is L or D.

30. The process of preparing a dipeptide having the structural formula

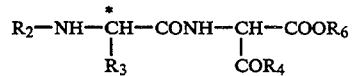

Formula V which comprises the steps of acylating with the corresponding acid chloride having the structural formula $R_4$—COCl    Formula VI using an alkali metal alkoxide in an inert solvent or solvent mixture the corresponding iminoester having the structural formula phenyl-$CR_7$=N—$CH_2$—$COOR_8$    Formula VII at a temperature in the range of −100° to 50° C. and then hydrolyzing at a temperature in the range of −100° to 50° C. the resulting corresponding acyliminoester having the structural formula phenyl-$CR_7$=N—CH($COR_4$)—$COOR_6$    Formula VIII with an aqueous mineral acid to form the corresponding acylaminoester having the structural formula $R_4$—CO—CH($NH_2$)—$COOR_6$    Formula IX and then condensing the acylaminoester of Formula IX with the corresponding amino acid having the structural formula

Formula X wherein
$R_2$ taken alone is a hydrogen atom;
$R_3$ taken alone is 1-methylethyl, 2-methylpropyl, 4-aminobutyl, phenylmethyl, 4-hydroxyphenylmethyl, pyridylmethyl, or (1H-indol-3-yl)methyl; or
$R_2$ taken together with N, CH and $R_3$ is (2,3,4,9-tetrahydro-1H-pyrido [3,4-b]indol-2,3-diyl;
$R_4$ is ethyl, propyl, 1-methylethyl, methylthiomethyl, ethylthiomethyl, phenyl, 4-hydroxyphenyl, pyridyl or 1H-indol-3-yl;
$R_6$ is methyl, ethyl or 1,1-dimethylethyl; and
$R_7$ is a hydrogen atom or phenyl; and
* is L or D.

31. The process of preparing an azole-fused peptide of Formula I wherein X is imido according to claim 1 and corresponding to a peptide having the structural formula

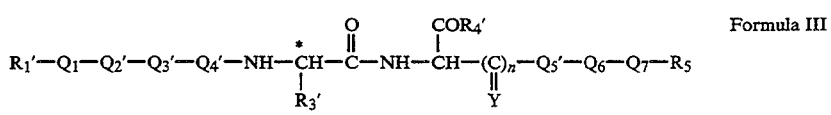

Formula III wherein
$Q_2'$ is L-prolyl or a direct linkage;
$Q_3'$ is L-prolyl, L-phenylalanyl or a direct linkage;
$Q_4'$ is L-prolyl, L-phenylalanyl or a direct linkage;

$Q_5'$ is L-phenylalanyl or a direct linkage;

$R_1'$ is the same as defined for $R_1$ in Formula I except that $R_1'$ cannot be a hydrogen atom when $Q_1$, $Q_2'$, $Q_3'$ and $Q_4'$ are each a direct linkage;

$R_3'$ is 1-methylethyl, 2-methylpropyl or phenylmethyl;

$R_4'$ is 1H-indol-3-yl; and $Q_1$, $Q_6$, $Q_7$, $R_5$, Y, n and I are the same as defined for Formula I, a dipeptide having the structural formula

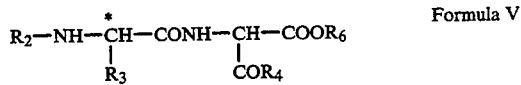

Formula V wherein $R_2$, $R_3$, $R_4$ and * are the same as defined for Formula I and $R_6$ is methyl, ethyl or 1,1-dimethylethyl or an aminoketoamide having the structural formula

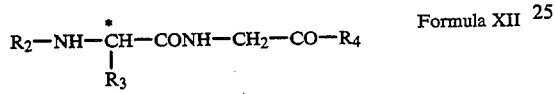

Formula XII wherein $R_2$, $R_3$, $R_4$ and * are the same as defined for Formula I which comprises the step of cyclizing the corresponding peptide of Formula III, dipeptide of Formula V or aminoketoamide of Formula XII with ammonia or an ammonium salt in acetic acid or a mixture of acetic acid and an inert solvent selected from the group consisting of aromatic hydrocarbons, alcohols, nitriles, amides and ethers with heating at a temperature from 50°–150° C.

32. The process of preparing an azole-fused peptide of Formula I according to claim which comprises the step of condensing the corresponding azole-fused peptide or compound of Formula I wherein any or all of $Q_1$, $Q_2$, $Q_3$, $Q_4$, $Q_5$, $Q_6$ and $Q_7$ is a direct linkage with any of the amino acid or peptide moieties $Q_1$, $Q_2$, $Q_3$, $Q_4$, $Q_5$, $Q_6$, $Q_7$, $Q_1$-$Q_2$, $Q_2$-$Q_3$, $Q_3$-$Q_4$, $Q_5$-$Q_6$, $Q_6$-$Q_7$, $Q_1$-$Q_2$-$Q_3$, $Q_2$-$Q_3$-$Q_4$, $Q_5$-$Q_6$-$Q_7$, and $Q_1$-$Q_2$-$Q_3$-$Q_4$ wherein $Q_1$, $Q_2$, $Q_3$, $Q_4$, $Q_5$, $Q_6$, and $Q_7$ of each said moiety is other than a direct linkage by a peptide forming method using a suitably carboxyl-activated derivative of the amino acid or peptide moiety intermediate, concomitantly protecting and deprotecting the N-terminal α-amino and the C-terminal carboxyl as required.

33. The process of preparing a compound of Formula I wherein Y is two separately bonded hydrogen atoms, n is 1 and $Q_1$, $Q_2$, $Q_3$, $Q_4$, $Q_5$, $Q_6$, and $Q_7$ are each a direct linkage which comprises the step of reducing the corresponding compound of Formula I wherein Y is oxo, n is 1 and $Q_1$, $Q_2$, $Q_3$, $Q_4$, $Q_5$, $Q_6$ and $Q_7$ are each a direct linkage with a boron or aluminum hydride selected from the group consisting of diborane, diisobutylaluminum hydride and lithium aluminum hydride in an inert ether solvent or solvent mixture at a temperature in the range of 0°–100° C.

34.

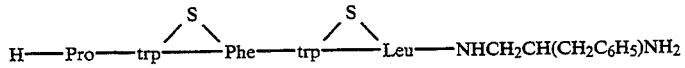

wherein

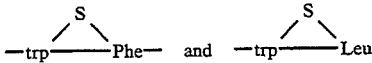

have the structural formula

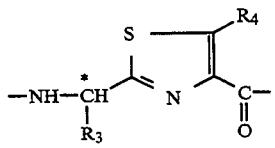

wherein $R_3$ is (1H-indol-3-yl)methyl in both, $R_4$ is phenyl and 1-methylethyl respectively and * is D in both or a pharmaceutically acceptable acid addition salt and/or solvate thereof.

* * * * *